US011542555B2

(12) United States Patent
Feldman et al.

(10) Patent No.: US 11,542,555 B2
(45) Date of Patent: *Jan. 3, 2023

(54) BAG3 AS A TARGET FOR THERAPY OF HEART FAILURE

(71) Applicant: TEMPLE UNIVERSITY OF THE COMMONWEALTH SYSTEM OF HIGHER EDUCATION, Philadelphia, PA (US)

(72) Inventors: Arthur M. Feldman, Wynnewood, PA (US); Douglas G. Tilley, Bryn Mawr, PA (US); Weizhong Zhu, Cockeysville, MD (US); Kamel Khalili, Bala Cynwyd, PA (US); Walter J. Koch, Broomall, PA (US)

(73) Assignee: TEMPLE UNIVERSITY OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/929,784

(22) Filed: May 21, 2020

(65) Prior Publication Data
US 2021/0017600 A1 Jan. 21, 2021

Related U.S. Application Data

(63) Continuation of application No. 15/115,807, filed as application No. PCT/US2015/013926 on Jan. 30, 2015, now Pat. No. 11,236,389.

(60) Provisional application No. 61/934,483, filed on Jan. 31, 2014.

(51) Int. Cl.
| | | |
|---|---|---|
| *C12Q 1/6883* | (2018.01) | |
| *G01N 33/68* | (2006.01) | |
| *A61K 48/00* | (2006.01) | |

(52) U.S. Cl.
CPC ....... *C12Q 1/6883* (2013.01); *G01N 33/6887* (2013.01); *G01N 33/6893* (2013.01); *A61K 48/00* (2013.01); *C12Q 2600/106* (2013.01); *C12Q 2600/156* (2013.01); *C12Q 2600/158* (2013.01); *G01N 2500/04* (2013.01); *G01N 2500/10* (2013.01); *G01N 2800/325* (2013.01); *G01N 2800/50* (2013.01)

(58) Field of Classification Search
CPC ......... G01N 33/6887; G01N 2800/325; A61K 48/00; C12Q 1/6883
See application file for complete search history.

(56) References Cited

U.S. PATENT DOCUMENTS

| | | |
|---|---|---|
| 2003/0175958 A1 | 9/2003 | Reed et al. |
| 2012/0137379 A1 | 5/2012 | Gao et al. |

FOREIGN PATENT DOCUMENTS

| | | |
|---|---|---|
| EP | 1323733 A1 | 7/2003 |
| WO | 2003/042397 A2 | 5/2003 |
| WO | 2010138263 A2 | 12/2010 |
| WO | 2012087835 A2 | 8/2012 |
| WO | 2012107580 A1 | 8/2012 |

OTHER PUBLICATIONS

Brancaccio, M., et al., Melusin gene therapy: a novel approach to fight familial dilated cardiomyopathy, European Heart Journal (Aug. 1, 2013); 34(suppl_I):3410.
Chamberlain, K., et al., Cardiac Gene Therapy with Adeno-Associated Virus-Based Vectors, Curr. Opin. Cardiol. (May 2017); 32(3):275-282.
Davis, J., et al., Lost in Transgenesis a User's Guide for Genetically Manipulating the Mouse in Cardiac Research, Circ. Res. (Aug. 31, 2012); 111:761-777.
Donahue, J. K., Cardiac gene therapy: a call for basic methods development, Lancet (Mar. 19, 2016); 387(10024):1137-1139.
Excerpt from the textbook 'Peptides and Proteins' (Feb. 28, 2002) by Shawn Doonan, including Chapter 1 'The Covalent Structures of Peptides and Proteins'.
Feldman, A.M., et al., Decreased Levels of BAG3 in a Family With a Rare Variant and in Idiopathic Dilated Cardiomyopathy, J. Cell. Physiol. (2014); 229(11):1697-1702.
Hajjar, R. and Ishikawa, K., Introducing Genes to the Heart: All About Delivery, Circ. Res. (Jan. 6, 2017); 120(1):33-35.
Kieserman, J.M., et al., Current Landscape of Heart Failure Gene Therapy, J. Am. Heart Assoc. (2019); 8(10):e012239.
Knezevic, T., et al., Abstracts from the 12th International Symposium on Neuro Virology, J. Neurovirol. (Oct. 8, 2013); 19(suppl_I):S44.
Kratlian, G.K. and Hajjar, R.J., Cardiac Gene Therapy: From Concept to Reality, Curr. Heart Fail. Rep. (Mar. 2012); 9(1):33-39.
Lavu, M., et al., Gene Therapy for Ischemic Heart Disease, J. Mal. Cell. Cardiol. (May 2011); 50(5):742-750.
Mamidi, R., et al., Cardiac myosin binding protein-C: a novel sarcomeric target for gene therapy, Eur. J. Physiol. (2014); 466:225-230.
Myers, V.D., et al., The Multifunctional Protein BAG3 a Novel Therapeutic Target in Cardiovascular Disease, JACC: Basic to Translational Science (Feb. 2018); 3(1):122-131.
Pleger, S.T., et al., Cardiac Calcium Handling on Trial Targeting the Failing Cardiomyocyte Signalosome, Circ. Res. (Jan. 3, 2014); 114:12-14.
Remme, W.J., Overview of the Relationship Between Ischemia and Congestive Heart Failure, Clin. Cardiol. (Jul. 2000); 23(Suppl. IV):IV-4-IV-8.
Rosati, A., et al., BAG3: a multifaceted protein that regulates major cell pathways, Cell Death and Disease (Apr. 2011); 2:e141.
Yamada, K.P., et al., Consideration of clinical translation of cardiac AAV gene therapy, Cell Gene Ther. Insights (Jun. 2020); 6(5):609-615.

(Continued)

*Primary Examiner* — Ekaterina Poliakova-Georgantas
(74) *Attorney, Agent, or Firm* — Pillsbury Winthrop Shaw Pittman LLP; Robert M. Bedgood

(57) ABSTRACT

Compositions are directed to BCL2-associated athanogene 3 (BAG3) molecules and agents which modulate expression of BAG3 molecules. Pharmaceutical composition for administration to patients, for example, patients with heart failure, comprise one or more BAG3 molecules or agents which modulate expression of BAG3. Methods of treatment and identifying candidate therapeutic agents are also provided.

17 Claims, 12 Drawing Sheets

Specification includes a Sequence Listing.

(56) References Cited

OTHER PUBLICATIONS

European Patent No. 3099333, Communication of a Notice of Opposition dated Aug. 23, 2021 (10 pages) and Opposition filed (24 pages).

Begay, et al., Exome Sequencing Identifies Bag3 Gene Mutation in Dilated Cardiomyopathy, Circulation, 2013, 128(22):Supplement, Abstract 15073, p. 1.

Citro, et al., Anti-Apoptotic BAG3 Gene in Tako-Tsubo Cardiomyopathy, Circulation, 2012, 126:Suppl 21, Abstract 13287:1-2.

Feldman, A.M., et al., BAG3 regulates contractility and $Ca^{2+}$ homeostasis in adult mouse ventricular myocytes, Journal of Molecular and Cellular Cardiology, 2016, 92:10-20.

Homma, et al., Cell Injury, Repair Aging and Apoptosis, BAG3 Deficiency Results in Fulminant Myopathy and Early Lethality, The American Journal of Pathology, 2006, 169(3):761-773.

Kimura, A., Molecular etiology and pathogenesis of idiopathic cardiomyopathy, J. Seizon and Life Sci., Mar. 2012, 22 Series B:45-52.

Nakai, H., Rapidly evolving adeno-associated virus vectors: increasing possibility of gene therapy with custom-made vectors, Drug Delivery System, 2009, 24-6:582-591; ISSN 0917-0138.

Norton, et al., Genome-wide Studies of Copy Number Variation and Exome Sequencing Identify Rare Variants in BAG3 as a Cause of Dilated Cardiomyopathy, The American Journal of Human Genetics, 2011, 88:273-282.

Odgerel, et al., Inheritance patterns and phenotypic features of myofibrillar myopathy associated with a BAG3 mutation, Neuromuscul Disord., 2010, 20(7):438-42.

Selcen, et al., Mutation in BAG3 causes severe dominant childhood muscular dystrophy, Ann. Neurol., 2009, 65(1):83-9.

Su, F., et al., Bcl-2-associated athanogene 3 protects the heart from ischemia/reperfusion injury, JCI Insight, 2016, 1(10):e90931 pp. 1-14.

Yin, et al., Endogenous microRNAs induced by heat-shock reduce myocardial infarction following ischemia-reperfusion in mice, FEBS Letters, 2008, 582:4137-4142.

Youn, et al., Bis deficiency results in early lethality with metabolic deterioration and involution of spleen and thymus, Am. J . . . Physiol. Endocrinol. Metab.,.2008, 295:E1349-E1357.

Arimura, T., et al., Dilated Cardiomyopathy-Associated BAG3 Mutations Impair Z-Disc Assembly and Enhance Sensitivity to Apoptosis in Cardiomyocytes, Human Mutation, 2011, 32:1481-1491.

FIG. 8

Exemplary Human BAG3 Polypeptide Sequence
(Genbank NP_004272.2; Public GI:14043024

```
  1 msaathspmm qvasgngdrd plppgweiki dpqtgwpffv dhnsrtttwn dprvpsegpk
 61 etpssangps reqsrlppar eghpvypqlr pgyipipvlh eqaenrqvhp fhvypqpgmq
121 rfrteaaaaa pqrsqsplrg mpettqpdkq cgqvaaaaaa qppashgper sqspaasdcs
181 sssssaslps sgrsslgshq lprgyisipv iheqnvtrpa aqpsfhqaqk thypaqqgey
241 qthqpvyhki qgddweprpl raaspfrssv qgassregsp arsstplhsp spirvhtvvd
301 rpqqpmthre tapvsqpenk peskpgpvgp elppghipiq virkevdskp vsqkppppse
361 kvevkvppap vpcpppspgp savpsspksv ateeraapst apaeatppkp geaeappkhp
421 gvlkveaile kvqgleqavd nfeqkktdkk ylmieeyitk ellaldsvdp egradvrqar
481 rdqvrkvqti lekleqkaid vpgqvqvyel qpsnleadqp lqaimemqav aadkgkknag
541 naedphtetq qpeatasats npssmtdtpg npsap (SEQ ID NO.1)
```

BAG3 AS A TARGET FOR THERAPY OF HEART FAILURE

CROSS-REFERENCE TO RELATED APPLICATIONS

This patent application is a continuation application of U.S. application Ser. No. 15/115,807, filed Aug. 1, 2016, which is the National Phase of International Application No. PCT/US2015/013926, filed Jan. 30, 2015, which designated the U.S. and that International Application was published under PCT Article 21(2) in English, which claims the benefit of priority to U.S. Provisional Application No. 61/934,483, filed Jan. 31, 2014. The entire contents of the foregoing applications are incorporated herein by reference, including all text, tables and drawings.

STATEMENT REGARDING FEDERALLY SPONSORED RESEARCH

This invention was made with U.S. government support under grant number P01HL091799 awarded by the National Institutes of Health. The U.S. government may have certain rights in the invention.

SEQUENCE LISTING

This application contains a Sequence Listing which has been submitted electronically in ASCII format and is hereby incorporated by reference in its entirety. Said ASCII copy, created on Oct. 12, 2020, is named "Oct2020SubRenovacor-0510900 ST25" and is 40 kB in size.

FIELD OF THE INVENTION

Embodiments of the invention are directed to compositions for the treatment of cardiac diseases or disorders, such as heart failure, cardiovascular diseases or disorders, or skeletal muscle diseases associated with Bcl-2 associated anthanogene-3 (BAG3) expression, and methods of treatment. Assays for the identification of novel therapeutic agents are also provided.

BACKGROUND

Heart failure (HF), secondary to systolic dysfunction and cardiac dilatation affects over 5 million individuals in the U.S. and is an important cause of both morbidity and mortality. Approximately 30% of these patients have non-ischemic disease or idiopathic dilated cardiomyopathy (IDC). Although in the majority of patients with IDC the causative factors have remained undefined, emerging evidence suggests that up to 35% of individuals with IDC have an affected first degree relative (Jefferies J L T J. *Lancet.* 2010; 375:752-762) and IDC can be associated with genetic abnormalities in 20-35% of individuals—leading to the use of the nomenclature familial dilated cardiomyopathy (FDC) (Judge D P et al, *Journal of Cardiovascular Translational Research.* 2008; 1:144-154; Hershberger R E et al. *Circulation. Cardiovascular Genetics.* 2010; 3:155-161). Indeed, mutations in more than 30 genes have been identified as causative factors (Hershberger R E, et al. *Circulation. Heart Failure.* 2009; 2:253-261) and the most common pattern of inheritance is autosomal dominant with reduced penetrance and variable expressivity (Morales A, Hershberger R E. *Current Cardiology Reports.* 2013; 15:375).

Mutations causing FDC are found in genes encoding a wide spectrum of proteins[6]; however, a large number of the mutations that cause FDC occur in genes that encode sarcomere proteins or the complex network of proteins in the Z-disc (Chang A N, Potter J D. *Heart Failure Reviews.* 2005; 10:225-235; Selcen D. Myofibrillar myopathies. *Neuromuscular disorders: NMD.* 2011; 21:161-171).

SUMMARY

Embodiments of the invention are directed to compositions for modulating the expression of Bcl-2 associated anthanogene-3 (BAG3) molecules, methods for identifying agents for treatment of cardiac diseases or disorders. In particular, these agents comprise expression vectors encoding Bcl-2 associated anthanogene-3 (BAG3) molecules, Bcl-2 associated anthanogene-3 (BAG3) nucleic acid sequences, Bcl-2 associated anthanogene-3 (BAG3) peptides or any other agent which modulates BAG3 expression. Such agents are identified by methods embodied herein. Conditions that are treated include, for example, heart failure, cardiomyopathy and the like. In some embodiments, the target tissues are cardiac tissues, such as for example, heart muscle.

Briefly, the results obtained herein have identified a rare and novel variant in a family with familial dilated cardiomyopathy. General embodiments of the invention are directed to treatment of patients identified as having variants of BAG3 molecules.

Patients with idiopathic dilated cardiomyopathy who did not have a mutation in the BAG3 gene were found to have half the normal level of BAG3, the same decrease that was found in the heart of the patient with the familial disease and the BAG3 mutation. Other general embodiments of the invention to treatment of patients with agents which modulate expression of BAG3 molecules, preferably resulting in overexpression of normal BAG3 molecules.

The results also showed that mice with heart failure due to aortic banding (a commonly used model for heart failure studies) had substantially less BAG3 than normal controls—and a reduction in BAG3 that mirrored that seen in humans.

Results also showed that when an AAV vector (AAV9) was administered in vivo, to over-express BAG3 in the heart, robust over-expression was observed. In other general embodiments, an agent comprises a cardiotropic vector expressing a BAG3 molecule. In some embodiments, the vector is an AAV9 vector.

It was also found that when the BAG3 protein was over-expressed in the hearts of mice with heart failure secondary to aortic banding (and low levels of BAG3) by using the AAV9 vector, normal left ventricular performance was reconstituted. These results provide evidence that BAG3 levels are decreased in the failing mouse heart and the AAV9 vector over-expressed BAG3 in the desired target in the heart resulting in the change in function comparable to a normal function.

Other aspects are described infra.

BRIEF DESCRIPTION OF THE DRAWINGS

FIG. 6A is a graph depicting heart weight to body weight ratios; FIG. 6B is a graph depicting contractility; FIG. 6C is a graph depicting BAG3 protein levels; FIG. 6D is an immunoblotting analysis of BAG3 protein levels.

FIG. 7A is a graph depicting ejection fraction; FIG. 7B is a graph depicting fractional shortening; FIG. 7C is a graph depicting end diastolic volume; FIG. 7D is a graph depicting end systolic volume; FIG. 7E is a graph depicting BAG3 protein levels; FIG. 7F is an immunoblotting analysis of BAG3 protein levels.

FIG. 8 shows the NCBI reference amino acid sequence for BAG3 (SEQ ID NO:1).

DETAILED DESCRIPTION

Figure 1:
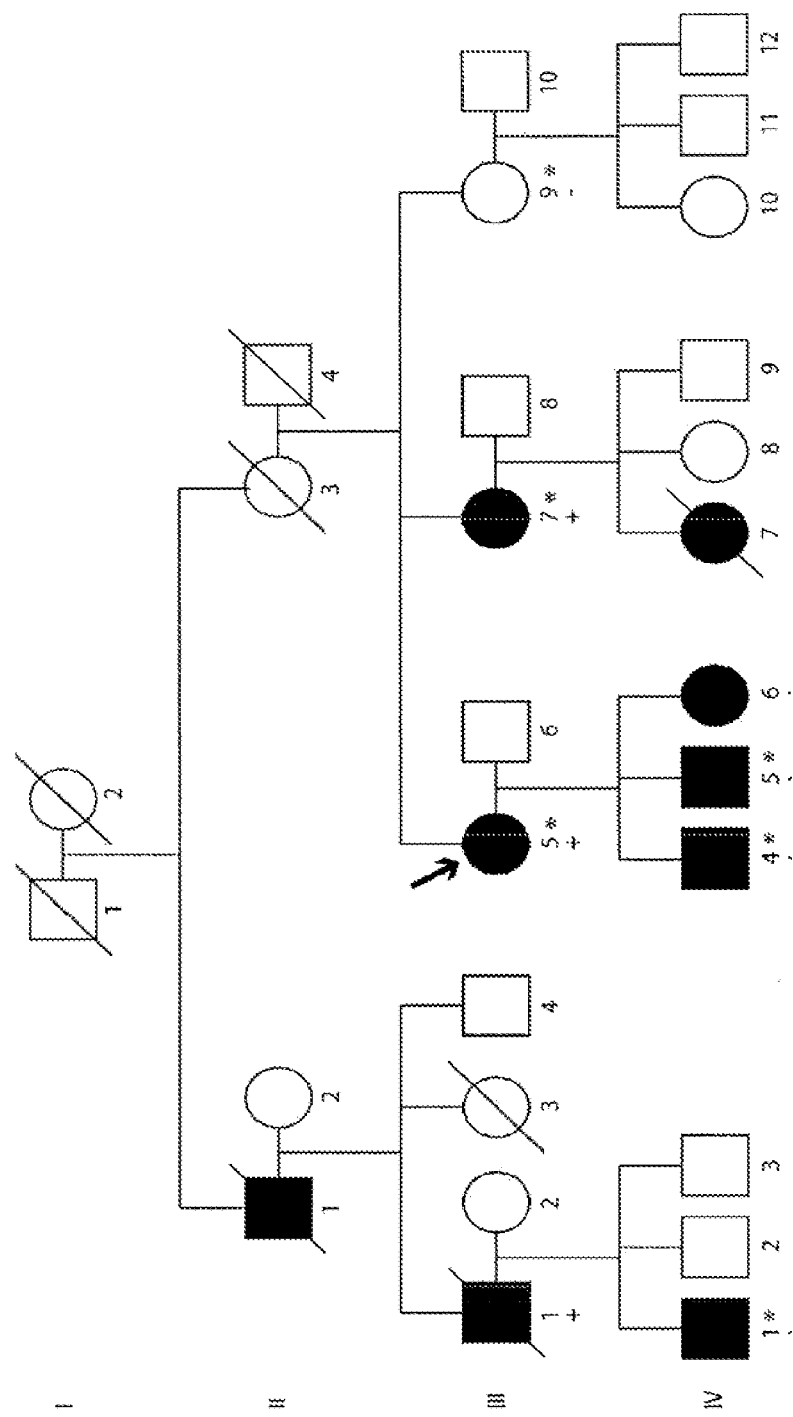
FIG. 1 is a schematic representation showing the BAG3-Associated Dilated Cardiomyopathy Pedigree. Males are represented by squares. Circles indicate females. Open symbols represent unaffected individuals and black symbols represent affected individuals. The presence or absence of the 10-nucleotide deletion in BAG3 is indicated by either a (+) or a (−) respectively. An arrow denotes the proband. An asterisk is used to denote individuals whose DNA was used for whole exome sequencing. A diagonal line is used to denote individuals who are deceased.

The present invention is based, in part, on the inventors' discovery of a novel BAG3 mutation in a family with adult-onset familial dilated cardiomyopathy (FDC). More specifically, the inventors have found that a novel 10 nucleotide deletion segregated in all affected individuals. Moreover, the inventors also found that levels of BAG3 protein were significantly reduced in hearts from unrelated patients with end-stage heart failure compared to non-failing controls. Further, the inventors have shown that, in a murine model of heart failure, administration of an AAV vector expressing BAG3, restored normal ventricular function. Accordingly, the invention features compositions that increase the expression of BAG3, methods of making such compositions, and methods of using such compositions to treat a subject, i.e., a patient suffering from dilated cardiomyopathy. Also featured are methods and compositions for diagnosis of heart failure, for example, idiopathic dilated cardiomyopathy (IDC).

Bcl-2 associated anthanogene-3 (BAG3), also known as BCL2-Associated Athanogene 3; MFM6; Bcl-2-Binding Protein Bis; CAIR-1; Docking Protein CAIR-1; BAG Family Molecular Chaperone Regulator 3; BAG-3; BCL2-Binding Athanogene 3; or BIS, is a cytoprotective polypeptide that competes with Hip-1 for binding to HSP 70. BAG3 function is illustrated in FIG. 8 and the mechanism for BAG3 involvement in cardiomyocyte function is illustrated in FIG. 9. The NCBI reference amino acid sequence for BAG3 can be found at Genbank under accession number NP_004272.2; Public GI:14043024. We refer to the amino acid sequence of Genbank accession number NP_004272.2; Public GI: 14043024 as SEQ ID NO: 1 as shown in FIG. 10. The NCBI reference nucleic acid sequence for BAG3 can be found at Genbank under accession number NM_004281.3 GI:62530382. We refer to the nucleic acid sequence of Genbank accession number NM_004281.3 GI:62530382 as (SEQ ID NO: 2). Other BAG3 amino acid sequences include, for example, without limitation, 095817.3 GI:12643665 (SEQ ID NO: 3); EAW49383.1 GI:119569768 (SEQ ID NO: 4); EAW49382.1 GI:119569767 (SEQ ID NO: 5); and CAE55998.1 GI:38502170 (SEQ ID NO: 6). The BAG3 polypeptide of the invention can be a variant of a polypeptide described herein, provided it retains functionality.

Vectors containing nucleic acids encoding a BAG3 polypeptide are provided herein.

A novel BAG3 mutation was identified in a family with adult-onset FDC. BAG3 protein levels were significantly decreased in unrelated patients with non-familial IDC providing evidence that altered levels of BAG3 protein participate in the progression of HE.

Embodiments are directed to compositions which modulate expression of Bcl-2 associated anthanogene-3 (BAG3) in vivo or in vitro. Modulation of BAG3 in patients in need of such therapy, include, patients with cardiac diseases or disorders, for example heart failure, or muscular-skeletal diseases or disorders. Embodiments are also directed to identification of novel compounds or agents which modulate BAG3 expression using assays which measure BAG3 expression.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention may be practiced without the theoretical aspects presented. Moreover, the theoretical aspects are presented with the understanding that Applicants do not seek to be bound by the theory presented.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Optional" or "optionally" means that the subsequently described circumstance may or may not occur, such that the description includes instances where the circumstance occurs and instances where it does not.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described (see, e.g., Curiel, D T, et al., *PNAS* 88: 8850-8854, 1991).

By "encoding" or "encoded", "encodes", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive promoter" is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

As used herein "BAG3", "BAG3 molecules", "BCL2-associated athanogene 3 (BAG3) genes", "BCL2-associated athanogene 3 (BAG3) molecules" are inclusive of all family members, mutants, cDNA sequences, alleles, fragments, species, coding and noncoding sequences, sense and antisense polynucleotide strands, etc. Similarly "BAG3", "BAG3 molecules", "BCL2-associated athanogene 3 (BAG3) molecules" also refer to BAG3 polypeptides or fragment thereof, proteins, variants, derivatives etc. The term "molecule", thus encompasses both the nucleic acid sequences and amino acid sequences of BAG3.

An "isolated nucleic acid or cDNA" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs, and refers to nucleic acid sequences in which one or more introns have been removed. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, for instance, DNA which is part of a hybrid gene encoding additional polypeptide sequences.

A "polynucleotide" means a single strand or parallel and anti-parallel strands of a nucleic acid. Thus, a polynucleotide may be either a single-stranded or a double-stranded nucleic acid.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

Unless otherwise indicated, the terms "peptide", "polypeptide" or "protein" are used interchangeably herein, although typically they refer to peptide sequences of varying sizes.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as "encoding" the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A "non-natural amino acid" refers to an amino acid that is not one of the 20 common amino acids or pyrolysine or selenocysteine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated, without user manipulation, into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids.

As used herein, the term "misexpression" refers to a non-wild type pattern of gene expression. It includes: expression at non-wild type levels, i.e., over- or underexpression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

By the term "modulate," it is meant that any of the mentioned activities of the compounds embodied herein, are, e.g., increased, enhanced, increased, agonized (acts as an agonist), promoted, decreased, reduced, suppressed blocked, or antagonized (acts as an antagonist). Modulation can increase activity more than 1-fold, 2-fold, 3-fold, 5-fold, 10-fold, 100-fold, etc., over baseline values. Modulation can also decrease its activity below baseline values.

As used herein, the term "agent" is meant to encompass any molecule, chemical entity, composition, drug, therapeutic agent, chemotherapeutic agent, or biological agent capable of preventing, ameliorating, or treating a disease or other medical condition. The term includes small molecule compounds, antisense reagents, siRNA reagents, antibodies, enzymes, peptides organic or inorganic molecules, natural or synthetic compounds and the like. An agent can be assayed in accordance with the methods of the invention at any stage during clinical trials, during pre-trial testing, or following FDA-approval.

As defined herein, a "therapeutically effective" amount of a compound or agent (i.e., an effective dosage) means an amount sufficient to produce a therapeutically (e.g., clinically) desirable result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

The terms "determining", "measuring", "evaluating", "detecting", "assessing" and "assaying" are used interchangeably herein to refer to any form of measurement, and include determining if an element is present or not. These terms include both quantitative and/or qualitative determinations. Assessing may be relative or absolute. "Assessing the presence of includes determining the amount of something present, as well as determining whether it is present or absent.

The term "assay" used herein, whether in the singular or plural shall not be misconstrued or limited as being directed to only one assay with specific steps but shall also include, without limitation any further steps, materials, various iterations, alternatives etc., that can also be used. Thus, if the term "assay" is used in the singular, it is merely for illustrative purposes.

A "label" or a "detectable label" is a composition detectable by spectroscopic, photochemical, biochemical, immunochemical, or chemical means. For example, useful labels include radio labeled molecules fluorophores, luminescent compounds, electron-dense reagents, enzymes (e.g., as commonly used in an ELISA), biotin, digoxigenin, or haptens and proteins which can be made detectable, e.g., by incorporating a label into the peptide or used to detect antibodies specifically reactive with the peptide.

The term "high-throughput screening" or "HTS" refers to a method drawing on different technologies and disciplines, for example, optics, chemistry, biology or image analysis to permit rapid, highly parallel biological research and drug discovery. HTS methods are known in the art and they are generally performed in multiwell plates with automated liquid handling and detection equipment; however it is envisioned that the methods of the invention may be practiced on a microarray or in a microfluidic system.

The term "library" or "drug library" as used herein refers to a plurality of chemical molecules (test compound), a plurality of nucleic acids, a plurality of peptides, or a plurality of proteins, organic or inorganic compounds, synthetic molecules, natural molecules, or combinations thereof.

As used herein, the term "target" or "target molecule" refers to any type of molecule, or structure to be detected, manipulated or characterized. The molecule can be an intracellular molecule, such as for example, nucleic acid sequences, peptides, structures (e.g. intracellular membranes, ribosomes, etc.), surface molecules (e.g. receptors), extracellular molecules (e.g. cytokines, enzymes, viral particles, organisms, biological samples and the like.

As used herein, "biological samples" include solid and body fluid samples. The biological samples used in the present invention can include cells, protein or membrane extracts of cells, blood or biological fluids such as ascites fluid or brain fluid (e.g., cerebrospinal fluid). Examples of solid biological samples include, but are not limited to, samples taken from tissues of the central nervous system, bone, breast, kidney, cervix, endometrium, head/neck, gallbladder, parotid gland, prostate, pituitary gland, muscle, esophagus, stomach, small intestine, colon, liver, spleen, pancreas, thyroid, heart, lung, bladder, adipose, lymph node, uterus, ovary, adrenal gland, testes, tonsils, thymus and skin, or samples taken from tumors. Examples of "body fluid samples" include, but are not limited to blood, serum, semen, prostate fluid, seminal fluid, urine, feces, saliva, sputum, mucus, bone marrow, lymph, and tears.

As used herein, "cardiac disease" refers to any type of heart disease including heart failure, heart muscle disease, cardiomyopathy, hypertrophic cardiomyopathy, dilated cardiomyopathy, atherosclerosis, coronary artery disease, ischemic heart disease, myocarditis, viral infection, wounds, hypertensive heart disease, valvular disease, congenital heart disease, myocardial infarction, congestive heart failure, arrhythmias, diseases resulting in remodeling of the heart, etc. Diseases of the heart can be due to any reason, such as for example, damage to cardiac tissue such as a loss of contractility (e.g., as might be demonstrated by a decreased ejection fraction).

Cardiac damage or disorder characterized by insufficient cardiac function includes any impairment or absence of a normal cardiac function or presence of an abnormal cardiac function. Abnormal cardiac function can be the result of disease, injury, and/or aging. As used herein, abnormal cardiac function includes morphological and/or functional abnormality of a cardiomyocyte, a population of cardiomyocytes, or the heart itself. Non-limiting examples of morphological and functional abnormalities include physical deterioration and/or death of cardiomyocytes, abnormal growth patterns of cardiomyocytes, abnormalities in the physical connection between cardiomyocytes, under- or over-production of a substance or substances by cardiomyocytes, failure of cardiomyocytes to produce a substance or substances which they normally produce, and transmission of electrical impulses in abnormal patterns or at abnormal times. Abnormalities at a more gross level include dyskinesis, reduced ejection fraction, changes as observed by echocardiography (e.g., dilatation), changes in EKG, changes in exercise tolerance, reduced capillary perfusion, and changes as observed by angiography. Abnormal cardiac function is seen with many disorders including, for example, ischemic heart disease, e.g., angina pectoris, myocardial infarction, chronic ischemic heart disease, hypertensive heart disease, pulmonary heart disease (cor pulmonale), valvular heart disease, e.g., rheumatic fever, mitral valve prolapse, calcification of mitral annulus, carcinoid heart disease, infective endocarditis, congenital heart disease, myocardial disease, e.g., myocarditis, dilated cardiomyopathy, hypertensive cardiomyopathy, cardiac disorders which result in congestive heart failure, and tumors of the heart, e.g., primary sarcomas and secondary tumors. Heart damage also includes wounds, such as for example, knife wound; biological (e.g. viral; autoimmune diseases) or chemical (e.g. chemotherapy, drugs); surgery; transplantation and the like.

As used herein the phrase "diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above. Diagnosis of a disease according to the present invention can be effected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject, as described in greater detail below.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

The terms "patient" or "individual" or "subject" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to a delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

Compositions

The most common cause of dilated cardiomyopathy and heart failure (HF) is ischemic heart disease, however, in a third of all patients the cause remains undefined and patients are diagnosed as having idiopathic dilated cardiomyopathy (IDC). The studies conducted herein, employed whole-exome sequencing to identify the causative variant in a large family with autosomal dominant transmission of dilated cardiomyopathy. Sequencing and subsequent informatics revealed a novel 10-nucleotide deletion in the BCL2-associated athanogene 3 (BAG3) gene ((Ch10:del 121436332_12143641: del. 1266_1275 [NM 004281]) that segregated with all affected individuals. The deletion predicted a shift in the reading frame with the resultant deletion of 135 amino acids from the C-terminal end of the protein. Consistent with genetic variants in genes encoding other sarcomeric proteins there was a considerable amount of genetic heterogeneity in the affected family members. Interestingly, it was also found that the levels of BAG3 protein were significantly reduced in the hearts from unrelated patients with end-stage HF undergoing cardiac transplantation when compared with non-failing controls. Diminished levels of BAG3 protein may be associated with both familial and non-familial forms of dilated cardiomyopathy. Accordingly, modulation of expression of BAG3 or amounts of BAG3 in a patient would be of great benefit.

In embodiments, a therapeutic agent for treatment of diseases associated with BAG3 and associated molecules and pathways thereof, modulates the expression or amounts of BAG3 in a cell.

In some embodiments, compositions comprise nucleic acid sequences of BCL2-associated athanogene 3 (BAG3), including without limitation, cDNA, sense and/or antisense sequences of BAG3.

In some embodiments, a composition comprises an expression vector having an isolated nucleic acid or cDNA sequence or synthetic nucleic acid sequence, encoding BCL2-associated athanogene 3 (BAG3) molecules. The term "nucleic acid sequence" will be used for the sake of brevity and will include, without limitation, isolated nucleic acid or cDNA sequences, synthesized or synthetic nucleic acid sequences, chimeric nucleic acid sequences, homologs, orthologs, variants, mutants or combinations thereof.

In some embodiments, a nucleic acid sequence of BAG3 comprises at least about a 50% sequence identity to wild type BAG3 or cDNA sequences thereof. In other embodiments, the BAG3 nucleic acid sequence comprises at least about 75%, 80%, 85%, 90%, 95%, 96%, 97%, 98%, 99% sequence identity to wild type BAG3 or cDNA sequences thereof.

In some embodiments, a nucleic acid sequence of BAG3 further comprises one or more mutations, substitutions, deletions, variants or combinations thereof.

In some embodiments, the homology, sequence identity or complementarity, between a BAG3 nucleic acid sequence comprising one or more mutations, substitutions, deletions, variants or combinations thereof and the native or wild type or cDNA sequences of BAG3 is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In one embodiment, an expression vector encodes a BCL2-associated athanogene 3 (BAG3) gene or cDNA sequences thereof, or modified sequences thereof. In one embodiment, the expression vector encodes a nucleic acid sequence comprising at least about 50% sequence identity to wild type BCL2-associated athanogene 3 (BAG3) or cDNA sequences thereof. In other embodiments, the nucleic acid sequence comprises at least about 75%, 80%, 85%, 90%, 95%, 96%, 97%, 98%, 99% sequence identity to wild type BCL2-associated athanogene 3 (BAG3) or cDNA sequences thereof.

A wide variety of host/expression vector combinations may be employed in expressing the BAG3 DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., Gene 67:31-40, 1988), pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2μ plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences; and the like.

A number of vectors are known to be capable of mediating transfer of gene products to mammalian cells, as is known in the art and described herein. A "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and vesicular stomatitis virus (VSV) and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; *BioTechniques,* 34: 167-171 (2003). A large variety of such vectors are known in the art and are generally available.

Suitable nucleic acid delivery systems include viral vector, typically sequence from at least one of an adenovirus, adenovirus-associated virus (AAV), helper-dependent adenovirus, retrovirus, or hemagglutinating virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., *J. Neurochem,* 64: 487 (1995); Lim, F., et al., in DNA Cloning: Mammalian Systems, D. Glover, Ed. (Oxford Univ. Press, Oxford England) (1995); Geller, A. I. et al., *Proc Natl. Acad. Sci.*: U.S.A.:90 7603 (1993); Geller, A. I., et al., *Proc Natl. Acad. Sci* USA: 87:1149 (1990)], Adenovirus Vectors [LeGal LaSalle et al., *Science,* 259:988 (1993); Davidson, et al., *Nat. Genet.* 3: 219 (1993); Yang, et al., *J. Virol.* 69: 2004 (1995)] and Adeno-associated Virus Vectors [Kaplitt, M. G., et al., *Nat. Genet.* 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors may be an indication for some invention embodiments. The adenovirus vector results in a shorter term expression (e.g., less than about a month) than adeno-associated vims (AAV), in some embodiments, may exhibit much longer expression. In some embodiments, the expression vector is an AAV9 vector. The particular vector chosen will depend upon the target cell and the condition being treated. The selection of appropriate promoters can readily be accomplished. Preferably, one would use a high expression promoter. An example of a suitable promoter is the 763-base-pair cytomegalovirus (CMV) promoter. The Rous sarcoma vims (RSV) (Davis, et al., *Hum Gene Ther* 4:151 (1993)) and MMT promoters may also be used. Certain proteins can expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an *E. coli* origin of replication. See, Sambrook, et al., Molecular Cloning: A Laboratory Manual, Cold Spring Harbor Laboratory press, (1989). The plasmid vector may also include a selectable marker such as the β-lactamase gene for ampicillin resistance, provided that the marker polypeptide does not adversely affect the metabolism of the organism being treated. The cassette can also be bound to a nucleic acid binding moiety in a synthetic delivery system, such as the system disclosed in WO 95/22618.

If desired, the polynucleotides of the invention may also be used with a microdelivery vehicle such as cationic liposomes and adenoviral vectors. For a review of the procedures for liposome preparation, targeting and delivery of contents, see Mannino and Gould-Fogerite, *BioTechniques*, 6:682 (1988). See also, Feigner and Holm, *Bethesda Res. Lab. Focus*, 11(2):21 (1989) and Maurer, R. A., *Bethesda Res. Lab. Focus*, 11(2):25 (1989).

Replication-defective recombinant adenoviral vectors, can be produced in accordance with known techniques. See, Quantin, et al., *Proc. Natl. Acad. Sci.* USA, 89:2581-2584 (1992); Stratford-Perricadet, et al., J. Clin. Invest., 90:626-630 (1992); and Rosenfeld, et al., Cell, 68:143-155 (1992).

Another delivery method is to use single stranded DNA producing vectors which can produce the BAG3 intracellularly, for example, cardiac tissues. See for example, Chen et al, *BioTechniques*, 34: 167-171 (2003), which is incorporated herein, by reference, in its entirety.

Expression of BAG3 may be controlled by any promoter/enhancer element known in the art, but these regulatory elements must be functional in the host selected for expression. In some embodiments, the promoter is a tissue specific promoter. Of particular interest are muscle specific promoters, and more particularly, cardiac specific promoters. These include the myosin light chain-2 promoter (Franz et al. (1994) *Cardioscience*, Vol. 5(4):235-43; Kelly et al. (1995) *J. Cell Biol.*, Vol. 129(2):383-396), the alpha actin promoter (Moss et al. (1996) *Biol. Chem.*, Vol. 271(49):31688-31694), the troponin 1 promoter (Bhaysar et al. (1996) *Genomics*, Vol. 35(1): 11-23); the $Na^+/Ca^{2+}$ exchanger promoter (Barnes et al. (1997) J. Biol. Chem., Vol. 272(17): 11510-11517), the dystrophin promoter (Kimura et al. (1997) *Dev. Growth Differ.*, Vol. 39(3):257-265), the alpha7 integrin promoter (Ziober and Kramer (1996) *J. Bio. Chem.*, Vol. 271(37):22915-22), the brain natriuretic peptide promoter (LaPointe et al. (1996) *Hypertension*, Vol. 27(3 Pt 2):715-22) and the alpha B-crystallin/small heat shock protein promoter (Gopal-Srivastava (1995) *J. Mol. Cell. Biol.*, Vol. 15(12):7081-7090), alpha myosin heavy chain promoter (Yamauchi-Takihara et al. (1989) *Proc. Natl. Acad. Sci. USA*, Vol. 86(10):3504-3508) and the ANF promoter (LaPointe et al. (1988) *J. Biol. Chem.*, Vol. 263(19):9075-9078).

Other promoters which may be used to control BAG3 gene expression include, but are not limited to, cytomegalovirus (CMV) promoter (U.S. Pat. Nos. 5,385,839 and 5,168,062), the SV40 early promoter region (Benoist and Chambon, 1981, *Nature* 290:304-310), the promoter contained in the 3' long terminal repeat of Rous sarcoma virus (Yamamoto, et al., *Cell* 22:787-797, 1980), the herpes thymidine kinase promoter (Wagner et al., *Proc. Natl. Acad. Sci.* U.S.A. 78:1441-1445, 1981), the regulatory sequences of the metallothionein gene (Brinster et al., *Nature* 296:39-42, 1982); prokaryotic expression vectors such as the β-lactamase promoter (Villa-Kamaroff, et al., *Proc. Natl. Acad. Sci.* U.S.A. 75:3727-3731, 1978), or the tac promoter (DeBoer, et al., *Proc. Natl. Acad. Sci.* U.S.A. 80:21-25, 1983); see also "Useful proteins from recombinant bacteria" in Scientific American, 242:74-94, 1980; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., *Cell* 38:639-646, 1984; Omitz et al., Cold Spring Harbor Symp. *Quant. Biol.* 50:399-409, 1986; MacDonald, *Hepatology* 7:425-515, 1987); insulin gene control region which is active in pancreatic beta cells (Hanahan, *Nature* 315:115-122, 1985), immunoglobulin gene control region which is active in lymphoid cells (Grosschedl et al., Cell 38:647-658, 1984; Adames et al., *Nature* 318:533-538, 1985; Alexander et al., *Mol. Cell. Biol.* 7:1436-1444, 1987), mouse mammary tumor virus control region which is active in testicular, breast, lymphoid and mast cells (Leder et al., *Cell* 45:485-495, 1986), albumin gene control region which is active in liver (Pinkert et al., *Genes and Devel.* 1:268-276, 1987), alpha-fetoprotein gene control region which is active in liver (Krumlauf et al., *Mol. Cell. Biol.* 5:1639-1648, 1985; Hammer et al., *Science* 235:53-58, 1987), alpha 1-antitrypsin gene control region which is active in the liver (Kelsey et al., *Genes and Devel.* 1:161-171, 1987), beta-globin gene control region which is active in myeloid cells (Mogram et al., *Nature* 315:338-340, 1985; Kollias et al., *Cell* 46:89-94, 1986), myelin basic protein gene control region which is active in oligodendrocyte cells in the brain (Readhead et al., *Cell* 48:703-712, 1987), myosin light chain-2 gene control region which is active in skeletal muscle (Sani, *Nature* 314:283-286, 1985), and gonadotropic releasing hormone gene control region which is active in the hypothalamus (Mason et al., *Science* 234:1372-1378, 1986).

Yeast expression systems can also be used according to the invention to express BAG3. For example, the non-fusion pYES2 vector (XbaI, SphI, ShoI, NotI, GstXI, EcoRI, BstXI, BamHl, SacI, KpnI, and HindIII cloning sites; Invitrogen) or the fusion pYESHisA, B, C (XbaI, SphI, ShoI, NotI, BstXI, EcoRI, BamHl, SacI, KpnI, and HindIII cloning sites, N-terminal peptide purified with ProBond resin and cleaved with enterokinase; Invitrogen), to mention just two, can be employed according to the invention. A yeast two-hybrid expression system can be prepared in accordance with the invention.

One preferred delivery system is a recombinant viral vector that incorporates one or more of the polynucleotides therein, preferably about one polynucleotide. Preferably, the viral o vector used in the invention methods has a pfu (plague forming units) of from about $10^8$ to about $5 \times 10^{10}$ pfu. In embodiments in which the polynucleotide is to be administered with a non-viral vector, use of between from about 0.1 nanograms to about 4000 micrograms will often be useful e.g., about 1 nanogram to about 100 micrograms.

In some embodiments, the vector is an adenovirus-associated viral vector (AAV), for example, AAV9. The term "AAV vector" means a vector derived from an adeno-associated virus serotype, including without limitation, AAV-1, AAV-2, AAV-3, AAV-4, AAV-5, AAV-6, AAV-7 and AAV-8. AAV vectors can have one or more of the AAV wild-type genes deleted in whole or part, preferably the rep and/or cap genes, but retain functional flanking ITR sequences. Despite the high degree of homology, the different serotypes have tropisms for different tissues. The receptor for AAV 1 is unknown; however, AAV 1 is known to transduce skeletal and cardiac muscle more efficiently than AAV2. Since most of the studies have been done with pseudotyped vectors in which the vector DNA flanked with AAV2 ITR is packaged into capsids of alternate serotypes, it is clear that the biological differences are related to the capsid rather than to the genomes. Recent evidence indicates that DNA expression cassettes packaged in AAV 1 capsids are at least 1 log 10 more efficient at transducing cardiomyocytes than those packaged in AAV2 capsids. In one embodiment, the viral delivery system is an adeno-associated viral delivery system. The adeno-associated virus can be of serotype I (AAV 1), serotype 2 (AAV2), serotype 3

(AAV3), serotype 4 (AAV4), serotype 5 (AAV5), serotype 6 (AAV6), serotype 7 (AAV7), serotype 8 (AAV8), or serotype 9 (AAV9).

Some skilled in the art have circumvented some of the limitations of adenovirus-based vectors by using adenovirus "hybrid" viruses, which incorporate desirable features from adenovirus as well as from other types of viruses as a means of generating unique vectors with highly specialized properties. For example, viral vector chimeras were generated between adenovirus and adeno-associated virus (AAV). These aspects of the invention do not deviate from the scope of the invention described herein.

Nucleic acids encoding the BAG3 proteins of the invention may be delivered to cardiac muscle by methods known in the art (see e.g., US Patent Appln. Publication No. US 2009/0209631). For example, cardiac cells of a large mammal may be transfected by a method that includes dilating a blood vessel of the coronary circulation by administering a vasodilating substance to said mammal prior to, and/or concurrent with, administering the nucleic acids. In some embodiments, the method includes administering the nucleic acids into a blood vessel of the coronary circulation in vivo, wherein nucleic acids are infused into the blood vessel over a period of at least about three minutes, wherein the coronary circulation is not isolated or substantially isolated from the systemic circulation of the mammal, and wherein the nucleic acids transfect cardiac cells of the mammal.

In some embodiments, the subject can be a human, an experimental animal, e.g., a rat or a mouse, a domestic animal, e.g., a dog, cow, sheep, pig or horse, or a non-human primate, e.g., a monkey. The subject may be suffering from a cardiac disorder, such as heart failure, ischemia, myocardial infarction, congestive heart failure, arrhythmia, transplant rejection and the like. In a preferred embodiment, the subject is suffering from heart failure. In another particular embodiment, the subject is suffering from arrhythmia. In one embodiment, the subject is a human. For example, the subject is between ages 18 and 65. In another embodiment, the subject is a non-human animal.

In one embodiment, the subject has or is at risk for heart failure, e.g. a non-ischemic cardiomyopathy, mitral valve regurgitation, ischemic cardiomyopathy, or aortic stenosis or regurgitation.

In some embodiments, transfection of cardiac cells with nucleic acid molecules encoding a BAG3 protein or BAG3 protein fused to an effector domain increases lateral ventricle fractional shortening. In some embodiments, the mammal is human and the disease is congestive heart failure. In some embodiments, the transfection of the cardiac cells increases lateral ventricle fractional shortening when measured about 4 months after said infusion by at least 25% as compared to lateral ventricle fractional shortening before infusion of the polynucleotide. In some embodiments, the transfection of the cardiac cells results in an improvement in a measure of cardiac function selected from the group consisting of expression of BAG3 protein, fractional shortening, ejection fraction, cardiac output, time constant of ventricular relaxation, and regurgitant volume.

A treatment can be evaluated by assessing the effect of the treatment on a parameter related to contractility. For example, SR Ca2+ATPase activity or intracellular $Ca^{2+}$ concentration can be measured. Furthermore, force generation by hearts or heart tissue can be measured using methods described in Strauss et al., *Am. J. Physiol.*, 262:1437-45, 1992, the contents of which are incorporated herein by reference.

Modified Nucleic Acid Sequences:

It is not intended that the present invention be limited by the nature of the nucleic acid employed, as long as they modulate the expression or quantities of BAG3 in a cell, or patient to whom, the nucleic acid composition is to be administered as a therapeutic agent. The nucleic acid may be DNA or RNA and may exist in a double-stranded, single-stranded or partially double-stranded form.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRE Press, Oxford, England)). RNAs may be produce in high yield via in vitro transcription using plasmids such as pGEM® T vector or SP65 (Promega Corporation, Madison, Wis.).

Accordingly, certain preferred nucleic acid sequences of this invention are chimeric nucleic acid sequences. "Chimeric nucleic acid sequences" or "chimeras," in the context of this invention, contain two or more chemically distinct regions, each made up of at least one nucleotide. These sequences typically contain at least one region of modified nucleotides that confers one or more beneficial properties (such as, for example, increased nuclease resistance, increased uptake into cells, increased binding affinity for the target).

Chimeric nucleic acid sequences of the invention may be formed as composite structures of two or more oligonucleotides, modified oligonucleotides, oligonucleosides and/or oligonucleotide mimetics. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

Specific examples of some modified nucleic acid sequences envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Examples of oligonucleotides with phosphorothioate backbones and those with heteroatom backbones, include without limitation: $CH_2$—NH—O—$CEH_2$, CH, —$N(CH_3)$—O—$CH_2$ [known as a methylene(methylimino) or MMI backbone], $CH_2$—O—$N(CH_3)$—$CH_2$, $CH_2$—$N(CH_3)$—$N(CH_3)$—$CH_2$ and O—$N(CH_3)$—CH—$CH_2$ backbones, wherein the native phosphodiester backbone is represented as O—P—O—$CH_1$). The amide backbones disclosed by De Mesmaeker et al. (1995) *Acc. Chem. Res.* 28:366-374 are also one example. In other embodiments, a nucleic acid sequence comprises morpholino backbone structures (Summerton and Weller, U.S. Pat. No. 5,034,506). In other embodiments, such as the peptide nucleic acid (PNA) backbone, the phosphodiester backbone of the nucleic acid sequence is replaced with a polyamide backbone, the nucleotides being bound directly or indirectly to the aza nitrogen atoms of the polyamide backbone (Nielsen et al. (1991) Science 254, 1497). Nucleic acid sequences may also comprise one or more substituted sugar moieties. Examples include: OH, SH, $SCH_3$, F, OCN, $OCH_3$ $OCH_3$, $OCH_3$ $O(CH_2)_nCH_3$, $O(CH_2)_nNH_2$ or $O(CH_2)_n$ $CH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; poly alky lamino; substituted silyl; a reporter group; an intercalator; a group for improving the pharmacokinetic properties of an oligonucleotide; or a group for improving the pharmacodynamic properties of an oligonucleotide and other substituents having similar properties. Other modifications include, for example: 2'-methoxyethoxy [2, —O— $CH_2$ $CH_2$ $OCH_3$, also known as 2'—O—(2-methoxyethyl)] (Martin et al., (1995) Helv. Chin. Acta, 78, 486), 2'-methoxy (2'—O—$CH_3$), 2,-propoxy (2'—$OCH_2$ $CH_2CH_3$) and 2'-fluoro (2'-F). Similar modifications may also be made at any positions on the oligonucleotide, the 2' or the 3' position of the sugar on the 3' terminal nucleotide and the 5' position of 5' terminal nucleotide. The nucleic acid sequences may also have sugar mimetics such as cyclobutyls in place of the pentofuranosyl group.

Preferred modified oligonucleotide backbones comprise, but are not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising S'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl intemucleoside linkages, mixed heteroatom and alkyl or cycloalkyl intemucleoside linkages, or one or more short chain heteroatomic or heterocyclic intemucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

The nucleic acid sequences may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' dcoxycytosinc and often referred to in the art as 5-Me-C), 5-hydroxy methyl cytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. (Komberg, A., DNA Replication, W.H. Freeman & Co., San Francisco, 1980, pp 75-77; Gebeyehu, G., (1987) et al. Nucl. Acids Res. 15:4513). A "universal" base known in the art, e.g., inosine, may be included.

Another modification involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety, cholic acid, a thioether, e.g., hexyl-5-tritylthiol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid. Nucleic acid sequences comprising lipophilic moieties, and methods for preparing such oligonucleotides are known in the art, for example, U.S. Pat. Nos. 5,138,045, 5,218,105 and 5,459,255.

It is not necessary for all positions in a given nucleic acid sequence to be uniformly modified, and in fact more than one of the aforementioned modifications may be incorporated in a single nucleic acid sequence or even at within a single nucleoside within an such sequences. The present invention also includes oligonucleotides which are chimeric oligonucleotides as hereinbefore defined.

In another embodiment, the BAGS nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

In another embodiment, the BAG3 nucleic acid sequences comprise one or more nucleotides substituted with locked nucleic acids (LNA). The LNA modified nucleic acid sequences may have a size similar to the parent or native sequence or may be larger or preferably smaller. It is preferred that such LNA-modified oligonucleotides contain less than about 70%, more preferably less than about 60%, most preferably less than about 50% LNA monomers and that their sizes are between about 1 and 25 nucleotides.

Antisense BAG3-Oligonucleotides:

In another preferred embodiment, the expression of BAG3 in a cell or patient is modulated by one or more target nucleic acid sequences which modulate the expression of BAG3, for example, transcriptional regulator elements.

In a preferred embodiment, an oligonucleotide comprises at least five consecutive bases complementary to a nucleic acid sequence, wherein the oligonucleotide specifically hybridizes to and modulates expression of BAG3 in vivo or in vitro. In another preferred embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the oligonucleotide. These compounds are then tested using the methods described herein to determine their ability to inhibit expression of a target nucleic acid.

In some embodiments, homology, sequence identity or complementarity, between the oligonucleotide and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another preferred embodiment, an oligonucleotide comprises combinations of phosphorothioate internucleotide linkages and at least one internucleotide linkage selected from the group consisting of: alkylphosphonate, phosphorodithioate, alkylphosphonothioate, phosphoramidate, carbamate, carbonate, phosphate triester, acetamidate, carboxymethyl ester, and/or combinations thereof.

In another preferred embodiment, an oligonucleotide optionally comprises at least one modified nucleobase comprising, peptide nucleic acids, locked nucleic acid (LNA) molecules, analogues, derivatives and/or combinations thereof.

An oligonucleotide is specifically hybridizable when binding of the compound to the target nucleic acid interferes with the normal function of the target nucleic acid to cause a loss of activity, and there is a sufficient degree of complementarity to avoid non-specific binding of the oligonucleotide to non-target nucleic acid sequences under conditions in which specific binding is desired. Such conditions include, i.e., physiological conditions in the case of in vivo assays or therapeutic treatment, and conditions in which assays are performed in the case of in vitro assays.

An oligonucleotide, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the oligonucleotide to non-target sequences under conditions in which specific binding is desired, i.e., under physiological conditions in the case of in vivo assays or therapeutic treatment, and in the case of in vitro assays, under conditions in which the assays are performed.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric oligonucleotides, particularly oligonucleotides, bind to target nucleic acid molecules and modulate the expression of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The oligonucleotides, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an oligonucleotide to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In another preferred embodiment, the antisense oligonucleotides bind to coding and/or non-coding regions of a target polynucleotide and modulate the expression and/or function of the target molecule.

In another preferred embodiment, the antisense oligonucleotides bind to natural antisense polynucleotides and modulate the expression and/or function of the target molecule. An example of a "function" can be one which inhibits a negative regulator of transcription, thus allowing for an increased expression of a desired molecule, such as, for example, BAGS.

In another preferred embodiment, the antisense oligonucleotides bind to sense polynucleotides and modulate the expression and/or function of the target molecule.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleobase positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in preferred embodiments, the gene expression is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

In another preferred embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs).

Small double-stranded RNA (dsRNA) may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In some embodiments, the ribonucleic acid sequence is specific for regulatory segments of the genome that control the transcription of BAG3. Thus a candidate therapeutic agent can be a dsRNA that activates the expression of BAG3 in a cell and is administered to a patient in need of treatment.

Peptides:

In another embodiment, a BAG3 peptide is encoded by a nucleic acid comprising a BCL2-associated athanogene 3 (BAG3) wild type, chimeric or cDNA sequences thereof. The peptide can also be a synthetic peptide of BCL2-associated athanogene 3 (BAG3).

It is to be understood that the peptide sequences are not limited to the native or cDNA sequences thereof, of BCL2-associated athanogene 3 (BAG3) molecules. The skilled artisan will recognize that conservative amino acid changes may be made, which although they alter the primary sequence of the protein or peptide, do not normally alter its function. Conservative amino acid substitutions typically include substitutions within the following groups: glycine, alanine, valine, isoleucine, leucine; aspartic acid, glutamic acid, asparagine, glutamine, serine, threonine, lysine, arginine, phenylalanine, tyrosine.

Conservative substitutions may also be made based on types of amino acids: aliphatic (valine, isoleucine, leucine, and alanine); charged (aspartic acid, glutamic acid, lysine, arginine, and histidine); aromatic residues (phenylalanine, tyrosine and tryptophan); and sulfur-containing (methionine and cysteine). Polypeptide sequences having at least about 68% identity, at least about 70% identity, or at least about 71% identity to a BCL2-associated athanogene 3 (BAG3) nucleic acid sequence, or cDNA sequences thereof.

The determination of percent identity between two nucleotide or amino acid sequences can be accomplished using a mathematical algorithm. For example, a mathematical algorithm useful for comparing two sequences is the algorithm of Karlin and Altschul (1990, *Proc. Natl. Acad. Sci.* USA 87:2264-2268), modified as in Karlin and Altschul (1993, *Proc. Natl. Acad. Sci.* USA 90:5873-5877). This algorithm is incorporated into the NBLAST and XBLAST programs of Altschul, et al. (1990, *J. Mol. Biol.* 215:403-410), and can be accessed, for example at the National Center for Biotechnology Information (NCBI) world wide web site having the universal resource locator http://blast (dot)ncbi(dot)nlm(dot)nih(dot)gov/blast.cgi/. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, *Nucleic Acids Res.* 25:3389-3402). Alternatively, PSI-Blast or PHI-Blast can be used to perform an iterated search which detects distant relationships between molecules and relationships between molecules which share a common pattern. When utilizing BLAST, Gapped BLAST, PSI-Blast, and PHI-Blast programs, the default parameters of the respective programs (e.g., XBLAST and NBLAST) can be used. In calculating percent identity, exact matches are typically counted.

Embodiments of the invention also include polynucleotides encoding hybrid proteins comprising BCL2-associated athanogene 3 (BAG3) polypeptide operatively fused directly or indirectly via peptide linker, to a second polypeptide sequence. Linker sequences are well known in the art. In one embodiment, a hybrid protein comprises a BAG3 polypeptide or a BAG3 polypeptide operatively fused to a detectable moiety, such as, a reporter polypeptide, wherein the reporter polypeptide is fused to the N- or C-terminal of the BAG3 polypeptide, directly or indirectly. Exemplary reporter polypeptides include luciferase (LUC), green fluorescent protein (GFP), and GFP derivatives.

Hybrid proteins comprising a BAG3 polypeptide or fragment thereof may be linked to other types of polypeptides, in addition to a reporter polypeptide, or in lieu of a reporter polypeptide. These additional polypeptides may be any amino acid sequence useful for the purification, identification, and/or therapeutic or prophylactic application of the peptide. In addition, the additional polypeptide can be a signal peptide, or targeting peptide, etc.

In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility of the polypeptide. In some embodiments sites are selected for substitution with a naturally encoded or non-natural amino acid in addition to another site for incorporation of a non-natural amino acid for the purpose of increasing the polypeptide solubility following expression in recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport through tissues or cell membranes, prodrug release or activation, size reduction, or other traits of the polypeptide.

The methods and compositions described herein include incorporation of one or more non-natural amino acids into a polypeptide. One or more non-natural amino acids may be incorporated at one or more particular positions which does not disrupt activity of the polypeptide. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, including but not limited to agonists, super-agonists, partial agonists, inverse agonists, antagonists, receptor binding modulators, receptor activity modulators, modulators of binding to binder partners, binding partner activity modulators, binding partner conformation modulators, dimer or multimer formation, no change to activity or property compared to the native molecule, or manipulating any physical or chemical property of the polypeptide such as solubility, aggregation, or stability. For example, locations in the polypeptide required for biological activity of a polypeptide can be identified using methods including, but not limited to, point mutation analysis, alanine scanning or homolog scanning methods. Residues other than those identified as critical to biological activity by methods including, but not limited to, alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

Candidate Agents and Screening Assays

The compositions embodied herein, can also be applied in the areas of drug discovery and target validation. The present invention comprehends the use of the nucleic acid sequences and peptides embodied herein, in drug discovery efforts to elucidate relationships that exist between Bcl-2 associated anthanogene-3 (BAG3) polynucleotides and a disease state, phenotype, or condition. These methods include detecting or modulating Bcl-2 associated anthanogene-3 (BAG3) polynucleotides comprising contacting a sample, tissue, cell, or organism with a compound, measuring the nucleic acid or protein level of Bcl-2 associated anthanogene-3 (BAG3) polynucleotides and/or a related phenotypic or chemical endpoint at some time after treatment, and optionally comparing the measured value to a non-treated sample or sample treated with a further compound of the invention.

The screening assays of the invention suitably include and embody, animal models, cell-based systems and non-cell based systems. The nucleic acid sequences and peptides embodied herein, are used for identifying agents of therapeutic interest, e.g. by screening libraries of compounds or otherwise identifying compounds of interest by any of a variety of drug screening or analysis techniques, or synthesis of novel compounds. The gene, allele, fragment, or oligopeptide thereof employed in such screening may be free in solution, affixed to a solid support, borne on a cell surface, or located intracellularly. The measurements are conducted as described in detail in the examples section which follows. In embodiments, screening candidate agents is performed to identify those which modulate the translation of BAG3.

The assays can be of an in vitro or in vivo format. In vitro formats of interest include cell-based formats, in which contact occurs e.g., by introducing the substrate in a medium, such as an aqueous medium, in which the cell is present. In yet other embodiments, the assay may be in vivo, in which a multicellular organism that includes the cell is employed. Contact of a targeting vector encoding the nucleic acid sequences embodied herein, with the target cell(s) may be accomplished using any convenient protocol. In those embodiments where the target cells are present as part of a multicellular organism, e.g., an animal, the vector is conveniently administered to (e.g., injected into, fed to, etc.) the multicellular organism, e.g., a whole animal, where administration may be systemic or localized, e.g., directly to specific tissue(s) and/or organ(s) of the multicellular organism.

Multicellular organisms of interest include, but are not limited to: insects, vertebrates, such as avian species, e.g., chickens; mammals, including rodents, e.g., mice, rates; ungulates, e.g., pigs, cows, horses; dogs, cats, primates, e.g., monkeys, apes, humans; and the like. As such, the target cells of interest include, but are not limited to: insects cells, vertebrate cells, particularly avian cells, e.g., chicken cells; mammalian cells, including murine, porcine, ungulate, ovine, equine, rat, dog, cat, monkey, and human cells; and the like.

The target cell comprising the BAG3 polynucleotides or BAG3 polypeptides is contacted with a test compound and the translation of BAG3 is evaluated or assessed by detecting the presence or absence of signal from a detectable moiety, for example, luciferase substrate, i.e., by screening the cell (either in vitro or in vivo) for the presence of a luciferase mediated luminescent signal. The detected signal is then employed to evaluate the translational and/or transcriptional activity of BAG3 in the presence of a test agent.

The luminescent signal may be detected using any convenient luminescent detection device. In certain embodiments, detectors of interest include, but are not limited to: photo-multiplier tubes (PMTs), avalanche photodiodes (APDs), charge-coupled devices (CCDs); complementary metal oxide semiconductors (CMOS detectors) and the like. The detector may be present in a signal detection device, e.g., luminometer, which is capable of detecting the signal once or a number of times over a predetermined period, as desired. Data may be collected in this way at frequent intervals, for example once every 10 ms, over the course of a given assay time period.

In certain embodiments, the subject methods are performed in a high throughput (HT) format. In the subject HT embodiments of the subject invention, a plurality of different cells are simultaneously assayed or tested. By simultaneously tested is meant that each of the cells in the plurality are tested at substantially the same time. In general, the number of cells that are tested simultaneously in the subject HT methods ranges from about 10 to 10,000, usually from about 100 to 10,000 and in certain embodiments from about 1000 to 5000. A variety of high throughput screening assays for determining the activity of candidate agent are known in the art and are readily adapted to the present invention, including those described in e.g., Schultz (1998) *BioorgMed Chem Lett* 8:2409-2414; Femandes (1998) *Curr Opin Chem Biol* 2:597-603; as well as those described in U.S. Pat. No. 6,127,133; the disclosures of which are herein incorporated by reference.

In some embodiments, a method of screening for agents which modulate translation and/or transcription of Bcl-2 associated anthanogene-3 (BAG3) comprises contacting a BAG3 molecule with an agent wherein the BAG3 molecule comprises an isolated nucleic acid or cDNA sequence of Bcl-2 associated anthanogene-3 (BAG3) operably linked to a detectable moiety, and at least one stop codon between the BAG3 and the detectable moiety; assessing the level of translation of the BAG3 in the absence of a candidate agent to obtain a reference level of translation and/or transcription, assessing the level of translation and/or transcription of BAG3 in the presence of the candidate agent to obtain a test level of translation and/or transcription, wherein the candidate agent is identified as an agent that increases translation and/or transcription if the test level of translation and/or transcription is greater than the reference level of translation and/or transcription.

In embodiments, the detectable moiety comprises: a luminescent moiety, a chemiluminescent moiety, a fluorescence moiety, a bioluminescent moiety, an enzyme, a natural or synthetic moiety.

Any method known in the art can be used to assess translation. In a preferred embodiment, translation is assessed using mammalian cells transfected with an expression vector comprising a nucleic acid of the invention. The transfection may be transient or the cells may stably transformed with the expression vector. A cell-based assay such as described in Butcher et al., 2007, *J Biol Chem.* 282:2853-28539 may be used. Alternatively, an in vitro translation assay may be used.

In the context of an expression vector, the vector can be readily introduced into a host cell, e.g., mammalian, bacterial, yeast or insect cell, by any method in the art. For example, the expression vector can be transferred into a host cell by physical, chemical or biological means.

Physical methods for introducing a polynucleotide into a host cell include calcium phosphate precipitation, lipofection, particle bombardment, microinjection, electroporation, photoporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

In the case where a non-viral delivery system is utilized, a preferred delivery vehicle is a liposome. The above-mentioned delivery systems and protocols therefore can be found in "Gene Targeting Protocols, 2ed.", Kmiec ed., Humana Press, Totowa, N.J., pp 1-35 (2002) and "Gene Transfer and Expression Protocols, Vol. 7, (Methods in Molecular Biology)," Murray ed., Humana Press, Totowa, N.J., pp 81-89 (1991).

Candidate Agents:

The methods can be practiced with any test compounds as candidate agents. Test compounds useful in practicing the inventive method may be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam, 1997, *Anticancer Drug Des.* 12:145).

Examples of methods for the synthesis of molecular libraries may be found in the art, for example, in: DeWitt et al., 1993, *Proc. Natl. Acad. Sci. USA* 90:6909-6913; Erb et al., 1994, *Proc. Natl. Acad. Sci. USA* 91:11422-11426; Zuckermann et al., 1994, *J. Med. Chem.* 37:2678-2685; Cho et al., 1992, *Science* 261:1303-1305; Carell et al., 1994, *Angew. Chem. Int. Ed. Engl.* 33:2059-2061; Carell et al., 1994, *Angew. Chem. Int. Ed. Engl.* 33:2061-2064; and Gallop et al., 1994, *J. Med. Chem.* 37:1233-1251.

Libraries of compounds may be presented in solution (e.g., Houghten, 1992, *Bio/Techniques* 13:412-421), or on beads (Lam, 1991, *Nature* 354:82-84), chips (Fodor, 1993, *Nature* 364:555-556), bacteria (U.S. Pat. No. 5,223,409), spores (U.S. Pat. Nos. 5,571,698; 5,403,484; and 5,223, 409), plasmids (Cull et al., 1992, *Proc. Natl. Acad. Sci. USA* 89:1865-1869), or phage (Scott and Smith, 1990, *Science*

249:386-390; Devlin, 1990, *Science* 249:404-406; Cwirla et al., 1990, *Proc. Natl. Acad. Sci. USA* 87:6378-6382; and Felici, 1991, *J Mol. Biol.* 222:301-310).

Commercially available libraries that may be screened include, but are not limited to, the TimTec Natural Product Library (NPL), NPL-640, and TimTec NDL-3000 library. Libraries comprising compounds modeled on polyamines (i.e., polyamine analogs) may also be screened.

In certain embodiments, the candidate agent is a small molecule or large molecule ligand. By small molecule ligand is meant a ligand ranging in size from about 50 to about 10,000 daltons, usually from about 50 to about 5,000 daltons and more usually from about 100 to about 1000 daltons. By large molecule is meant a ligand ranging in size from about 10,000 daltons or greater in molecular weight.

The method may be practiced iteratively using different concentrations of a test candidate and/or different testing conditions, such as duration of reaction time. Test candidates that are identified by the method can be further tested by conventional methods in the art to verify specificity, dose dependency, efficacy in vivo, and the like. Test candidates may serve as lead compounds for developing additional test candidates.

As indicated above, the present invention finds use in monitoring translational and/or transcriptional activity of BAG3 in an assay wherein the test is conducted using cells. In these embodiments, the cells are cultured under specific user-defined conditions (e.g., in the presence or absence of a cytokine, nutrient and/or candidate therapeutic agent), and monitored for emitted light.

A prototype compound or agent may be believed to have therapeutic activity on the basis of any information available to the artisan. For example, a prototype agent may be believed to have therapeutic activity on the basis of information contained in the Physician's Desk Reference. In addition, by way of non-limiting example, a compound may be believed to have therapeutic activity on the basis of experience of a clinician, structure of the compound, structural activity relationship data, EC50, assay data, IC50 assay data, animal or clinical studies, or any other basis, or combination of such bases.

A therapeutically-active compound or agent is an agent that has therapeutic activity, including for example, the ability of the agent to induce a specified response when administered to a subject or tested in vitro. Therapeutic activity includes treatment of a disease or condition, including both prophylactic and ameliorative treatment. Treatment of a disease or condition can include improvement of a disease or condition by any amount, including prevention, amelioration, and elimination of the disease or condition. Therapeutic activity may be conducted against any disease or condition, including in a preferred embodiment against any disease or disorder associated with damage by reactive oxygen intermediates. In order to determine therapeutic activity any method by which therapeutic activity of a compound may be evaluated can be used. For example, both in vivo and in vitro methods can be used, including for example, clinical evaluation, $EC_{50}$, and $IC_{50}$ assays, and dose response curves.

Candidate compounds for use with an assay of the present invention or identified by assays of the present invention as useful pharmacological agents can be pharmacological agents already known in the art or variations thereof or can be compounds previously unknown to have any pharmacological activity. The candidate compounds can be naturally occurring or designed in the laboratory. Candidate compounds can comprise a single diastereomer, more than one diastereomer, or a single enantiomer, or more than one enantiomer.

Candidate compounds can be isolated, from microorganisms, animals or plants, for example, and can be produced recombinantly, or synthesized by chemical methods known in the art. If desired, candidate compounds of the present invention can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries. The other four approaches are applicable to polypeptide, non-peptide oligomers, or small molecule libraries of compounds and are preferred approaches in the present invention. See Lam, *Anticancer Drug Des.* 12: 145-167 (1997).

In an embodiment, the present invention provides a method of identifying a candidate compound as a suitable prodrug. A suitable prodrug includes any prodrug that may be identified by the methods of the present invention. Any method apparent to the artisan may be used to identify a candidate compound as a suitable prodrug.

In another aspect, the present invention provides methods of screening candidate compounds for suitability as therapeutic agents. Screening for suitability of therapeutic agents may include assessment of one, some or many criteria relating to the compound that may affect the ability of the compound as a therapeutic agent. Factors such as, for example, efficacy, safety, efficiency, retention, localization, tissue selectivity, degradation, or intracellular persistence may be considered. In an embodiment, a method of screening candidate compounds for suitability as therapeutic agents is provided, where the method comprises providing a candidate compound identified as a suitable prodrug, determining the therapeutic activity of the candidate compound, and determining the intracellular persistence of the candidate compound. Intracellular persistence can be measured by any technique apparent to the skilled artisan, such as for example by radioactive tracer, heavy isotope labeling, or LCMS.

In screening compounds for suitability as therapeutic agents, intracellular persistence of the candidate compound is evaluated. In a preferred embodiment, the agents are evaluated for their ability to modulate the translation of compositions embodied herein, over a period of time in response to a candidate therapeutic agent.

In another preferred embodiment, soluble and/or membrane-bound forms of compositions embodied herein, e.g. proteins, mutants or biologically active portions thereof, can be used in the assays for screening candidate agents. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON™ X-100, TRITON™ X-114, THESIT™, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays can also be used and involve preparing a reaction mixture which includes BAG3 molecules (nucleic acids or peptides) comprising a bioluminescent moiety and the test compound under conditions and time periods to allow the measurement of the translational and/or transcriptional activity over time, and concentrations of test agents.

In other embodiments, a candidate agent is an antisense oligonucleotide. In embodiments, BAG3 expression (e.g., protein) in a sample (e.g., cells or tissues in vivo or in vitro) treated using an antisense oligonucleotide of the invention is evaluated by comparison with BAG3 expression in a control sample. For example, the translation of the BAG3 is monitored by the signal emitted by the detectable moiety and compared with that in a mock-treated or untreated sample. Alternatively, comparison with a sample treated with a control antisense oligonucleotide (e.g., one having an altered or different sequence) can be made depending on the information desired. In another embodiment, a difference in the translational and/or transcriptional activity in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In some embodiments, the level of BAG3 protein, in a sample treated with an antisense oligonucleotide, is increased or decreased by about 1.25-fold to about 10-fold or more relative to an untreated sample or a sample treated with a control nucleic acid. Preferably, the level or amount of BAG3 is increased. In embodiments, the level of BAG3 protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more. In embodiments, it is preferable that the level or amount of BAG3 is increased.

Microarrays:

Identification of a nucleic acid sequence capable of binding to a target molecule can be achieved by immobilizing a library of nucleic acids onto the substrate surface so that each unique nucleic acid is located at a defined position to form an array. In general, the immobilized library of nucleic acids are exposed to a biomolecule or candidate agent under conditions which favored binding of the biomolecule to the nucleic acids. The nucleic acid array would then be analyzed by the methods embodied herein to determine which nucleic acid sequences bound to the biomolecule. Preferably the biomolecules would carry a pre-determined label for use in detection of the location of the bound nucleic acids.

An assay using an immobilized array of BAG3 nucleic acid sequences may be used for determining the sequence of an unknown nucleic acid; single nucleotide polymorphism (SNP) analysis; analysis of BAG3 gene expression patterns from a particular species, tissue, cell type, etc.; gene identification; etc.

In further embodiments, oligonucleotides or longer fragments derived from any of the BAG3 polynucleotide sequences, may be used as targets in a microarray. The microarray can be used to monitor the identity and/or expression level of large numbers of genes and gene transcripts simultaneously to identify genes with which target genes or its product interacts and/or to assess the efficacy of candidate therapeutic agents in regulating expression products of genes that mediate, for example, neurological disorders. This information may be used to determine gene function, and to develop and monitor the activities of therapeutic agents.

Microarrays may be prepared, used, and analyzed using methods known in the art (see, e.g., Brennan et al., 1995, U.S. Pat. No. 5,474,796; Schena et al., 1996, Proc. Natl. Acad. Sci. U.S.A. 93: 10614-10619; Baldeschweiler et al., 1995, PCT application WO95/251116; Shalon, et al., 1995, PCT application WO95/35505; Heller et al., 1997, Proc. Natl. Acad. Sci. U.S.A. 94: 2150-2155; and Heller et al., 1997, U.S. Pat. No. 5,605,662). In other embodiments, a microarray comprises BAG3 peptides, or other desired molecules which can be assayed to identify a candidate agent.

In another preferred embodiment a method for screening candidate agents for the treatment or prevention of a cardiac disease or disorder comprises contacting a sample with a candidate therapeutic agent and measuring the effects the agent has on a target. For example, the agent may regulate BAG3 expression and the agent can then be further studied for any possible therapeutic effects (increase or decrease parameter being monitored e.g. expression). An abnormal expression state may be caused by pathology such as heart failure, disease, cancer, genetic defects and/or a toxin.

Antibodies.

Figure 2A:
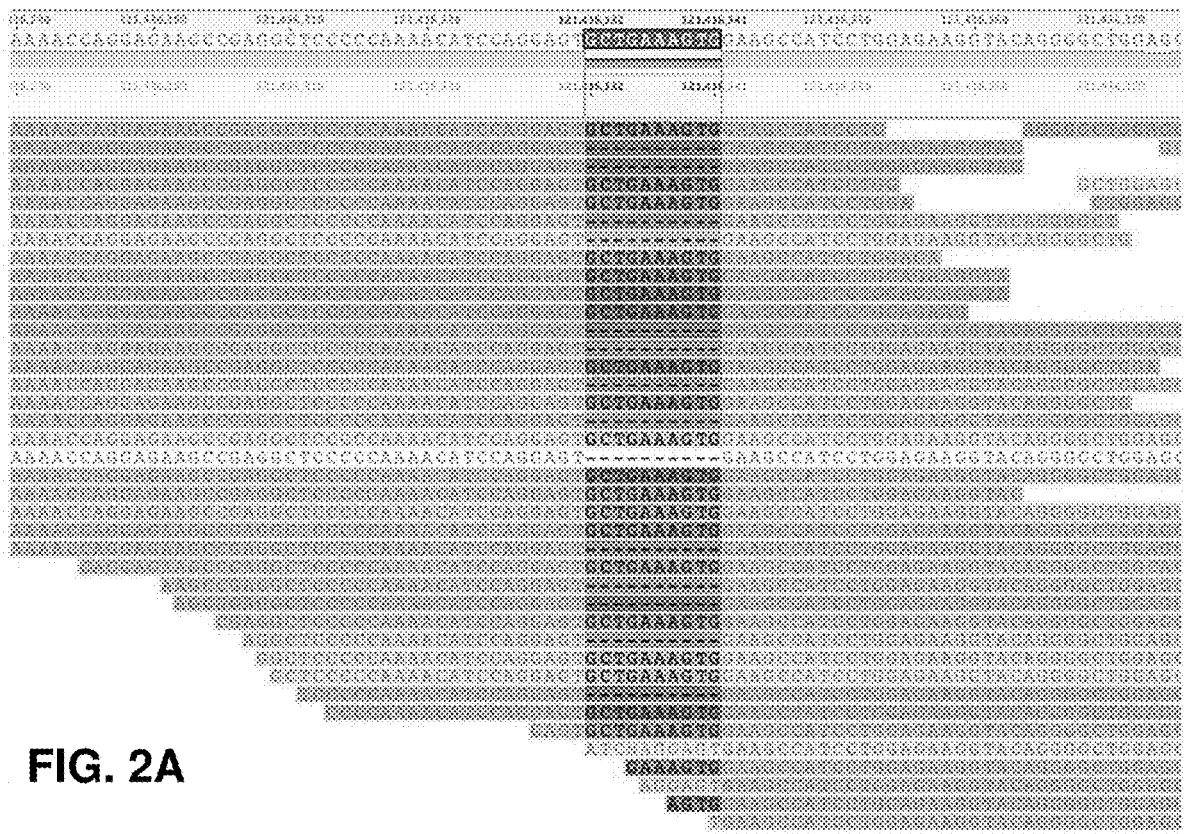
FIG. 2A is a schematic representation showing the sequencing alignment for BAG3 10-nucleotide deletion (SEQ ID NO:9-49).
Figure 2B:
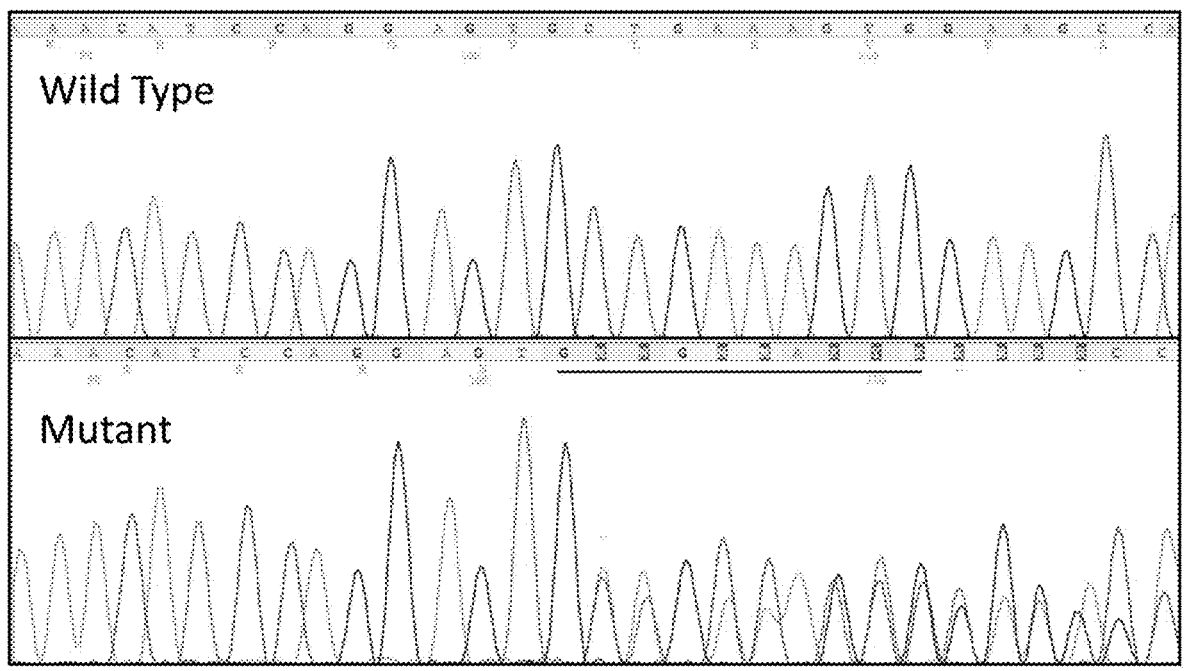
FIG. 2B is a schematic representation showing the representative Sanger sequencing of the deletion in the BAG3 gene in an affected individual (SEQ ID NO:50-51).

Useful diagnostic assays can include one or more antibodies that specifically bind BAG3. In some embodiments, the antibody specifically binds a mutant BAG3, for example, the BAG3 polypeptide disclosed herein having the 10 amino acid deletion as shown in FIG. 2. We use the term antibody to broadly refer to immunoglobulin-based binding molecules, and the term encompasses conventional antibodies (e.g., the tetrameric antibodies of the G class (e.g., an IgG1)), fragments thereof that retain the ability to bind their intended target (e.g., an Fab' fragment), and single chain antibodies (scFvs). The antibody may be polyclonal or monoclonal and may be produced by human, mouse, rabbit, sheep or goat cells, or by hybridomas derived from these cells. The antibody can be humanized, chimeric, or bi-specific.

The antibodies can assume various configurations and encompass proteins consisting of one or more polypeptides substantially encoded by immunoglobulin genes. Any one of a variety of antibody structures can be used, including the intact antibody, antibody multimers, or antibody fragments or other variants thereof that include functional, antigen-binding regions of the antibody. We may use the term "immunoglobulin" synonymously with "antibody." The antibodies may be monoclonal or polyclonal in origin. Regardless of the source of the antibody, suitable antibodies include intact antibodies, for example, IgG tetramers having two heavy (H) chains and two light (L) chains, single chain antibodies, chimeric antibodies, humanized antibodies, complementary determining region (CDR)-grafted antibodies as well as antibody fragments, e.g. Fab, Fab', F(ab')2, scFv, Fv, and recombinant antibodies derived from such fragments, e.g., camelbodies, microantibodies, diabodies and bispecific antibodies.

An intact antibody is one that comprises an antigen-binding variable region ($V_H$ and $V_L$) as well as a light chain constant domain ($C_L$) and heavy chain constant domains, $C_{H1}$, $C_{H2}$ and $C_{H3}$. The constant domains may be native sequence constant domains (e.g. human native sequence constant domains) or amino acid sequence variants thereof. As is well known in the art, the $V_H$ and $V_L$ regions are further subdivided into regions of hypervariability, termed "complementarity determining regions" (CDRs), interspersed with the more conserved framework regions (FRs).

An anti-BAGS antibody can be from any class of immunoglobulin, for example, IgA, IgG, IgE, IgD, IgM (as well as subtypes thereof (e.g., $IgG_1$, $IgG_2$, $IgG_3$, and $IgG_4$)), and the light chains of the immunoglobulin may be of types kappa or lambda. The recognized human immunoglobulin genes include the kappa, lambda, alpha ($IgA_1$ and $IgA_2$), gamma ($IgG_1$, $IgG_2$, $IgG_3$, $IgG_4$), delta, epsilon, and mu constant region genes, as well as the many immunoglobulin variable region genes.

The term "antigen-binding portion" of an immunoglobulin or antibody refers generally to a portion of an immunoglobulin that specifically binds to a target, in this case, an epitope comprising amino acid residues on a BAG3 polypeptide. An antigen-binding portion of an immunoglobulin is therefore a molecule in which one or more immunoglobulin chains are not full length, but which specifically binds to a cellular target. Examples of antigen-binding portions or fragments include: (i) an Fab fragment, a monovalent fragment consisting of the VLC, VHC, CL and CHI domains; (ii) a $F(ab')_2$ fragment, a bivalent fragment comprising two Fab fragments linked by a disulfide bridge at the hinge region; (iii) a Fv fragment consisting of the VLC and VHC domains of a single arm of an antibody, and (v) an isolated CDR having sufficient framework to specifically bind, e.g., an antigen binding portion of a variable region. An antigen-binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv). Such scFvs can be a target agent of the present invention and are encompassed by the term "antigen-binding portion" of an antibody.

An "Fv" fragment is the minimum antibody fragment that contains a complete antigen-recognition and binding site. This region consists of a dimer of one heavy chain and one light chain variable domain in tight, con-covalent association. It is in this configuration that three hypervariable regions of each variable domain interact to define an antigen-binding site on the surface of the $V_H$-$V_L$ dimer. While six hypervariable regions confer antigen-binding specificity, even a single variable domain (or half of an Fv comprising only three hypervariable regions specific for an antigen) has the ability to recognize and bind antigen, although at a lower affinity than the entire binding site. To improve stability, the VH-VL domains may be connected by a flexible peptide linker such as $(GlY_4Ser)_3$ (SEQ ID NO:7) to form a single chain Fv or scFV antibody fragment or may be engineered to form a disulfide bond by introducing two cysteine residues in the framework regions to yield a disulfide stabilized Fv (dsFv). Fragments of antibodies are suitable for use in the methods provided so long as they retain the desired specificity of the full-length antibody and/or sufficient specificity to specifically bind to a BAG3 polypeptide.

The compositions of the present invention include antibodies that (1) exhibit a threshold level of binding activity; and/or (2) do not significantly cross-react with known related polypeptide molecules. The binding affinity of an antibody can be readily determined by one of ordinary skill in the art, for example, by Scatchard analysis (Scatchard, Ann. NY Acad, Sci. 51:660-672 (1949)).

In some embodiments, the anti-BAG3 antibodies can bind to their target epitopes or mimetic decoys at least 1.5-fold, 2-fold, 5-fold 10-fold, 100-fold, $10^3$-fold, $10^4$-fold, $10^5$-fold, $10^6$-fold or greater for the target anti-BAG3 than to other proteins predicted to have some homology to BAG3.

In some embodiments the anti-BAG3 antibodies bind with high affinity of $10^{-4}$ M or less, $10^{-7}$ M or less, $10^{-9}$ M or less or with subnanomolar affinity (0.9, 0.8, 0.7, 0.6, 0.5, 0.4, 0.3, 0.2, 0.1 nM or even less). In some embodiments the binding affinity of the anti-BAG3 antibodies for their respective targets is at least $1\times10^6$ Ka. In some embodiments the binding affinity of the anti-BAG3 antibodies for BAG3 is at least $5\times10^6$ Ka, at least $1\times10^7$ Ka, at least $2\times10^7$ Ka, at least $1\times10^8$ Ka, or greater. Antibodies may also be described or specified in terms of their binding affinity to BAG3. In some embodiments binding affinities include those with a Kd less than $5\times10^{-2}$ M, $10^{-2}$ M, $5\times10^{-3}$ M, $10^{-3}$ M, $5\times10^{-3}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M, or less.

In some embodiments, the antibodies do not bind to known related polypeptide molecules; for example, they bind BAG3, but not known related polypeptides. In some embodiments, the antibodies specifically bind to a mutant BAG3 polypeptide, for example a BAG3 polypeptide having the ten base pair deletion as shown in FIG. 2, but not to a wild type BAG3 polypeptide. Antibodies may be screened against known related polypeptides to isolate an antibody population that specifically binds BAG3.

The diagnostic assays of the invention can include concurrent immunoelectrophoresis, radioimmunoassay (RIA), radioimmunoprecipitation, enzyme-linked immunosorbent assay (ELISA), dot blot or Western blot assay, inhibition or competition assay, and sandwich assay. The anti-BAG3 antibodies can include a tag, which may also be referred to as a reporter or marker (e.g., a detectable marker). A detectable marker can be any molecule that is covalently linked to the anti-BAG3 antibody or a biologically active fragment thereof that allows for qualitative and/or quantitative assessment of the expression or activity of the tagged peptide. The activity can include a biological activity, a physico-chemical activity, or a combination thereof. Both the form and position of the detectable marker can vary, as long as the labeled antibody retains biological activity. Many different markers can be used, and the choice of a particular marker will depend upon the desired application. Labeled anti-BAG3 antibodies can be used, for example, for assessing the levels of BAG3 or a mutant BAG3 in a biological sample, e.g., urine, saliva, cerebrospinal fluid, blood or a biopsy sample or for evaluation the clinical response to a cardiovascular therapeutic, for example, the BAG3 constructs described above.

Exemplary detectable labels include a radiopaque or contrast agents such as barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride. Alternatively or in addition, the detectable label can be a fluorescent label, for example, fluorescein isothiocyanate, rhodamine, phycoerytherin, phycocyanin, allophycocyanin, o-phthaldehyde and fluorescamine; a chemiluminescent compound selected from the group consisting of luminol, isoluminol, an aromatic acridinium ester, an imidazole, an acridinium salt and an oxalate ester; a liposome or dextran; or a bioluminescent compound such as luciferin, luciferase and aequorin.

Suitable markers include, for example, enzymes, photoaffinity ligands, radioisotopes, and fluorescent or chemiluminescent compounds. Methods of introducing detectable markers into peptides are well known in the art. Markers can be added during synthesis or post-synthetically. Recombinant anti-BAG3 antibodies or biologically active variants thereof can also be labeled by the addition of labeled precursors (e.g., radiolabeled amino acids) to the culture medium in which the transformed cells are grown. In some embodiments, analogues or variants of peptides can be used in order to facilitate incorporation of detectable markers. For example, any N-terminal phenylalanine residue can be replaced with a closely related aromatic amino acid, such as tyrosine, that can be easily labeled with 125I. In some embodiments, additional functional groups that support effective labeling can be added to the fragments of an anti-BAG3 antibody or biologically active variant thereof. For example, a 3-tributyltinbenzoyl group can be added to the N-terminus of the native structure; subsequent displacement of the tributyltin group with 125I will generate a radiolabeled iodobenzoyl group.

Any art-known method can be used for detecting such labels, for example, positron-emission tomography (PET), SPECT imaging, magnetic resonance imaging, X-ray; or is detectable by ultrasound.

In other preferred embodiments, a method of treating a patient having a cardiac disease or disorder, wherein the patient has decreased BAG3 levels as compared to a baseline level, comprising administering a pharmaceutical composition comprising a therapeutically effective amount of at least one BAG3 inducing agent wherein the agent increases expression of the BAG3 molecule.

In other embodiments, a method of preventing or treating a subject at risk of or suffering from a cardiac disease or disorder comprising: administering to the subject a pharmaceutical composition comprising a therapeutically effective amount of at least one agent which modulates, expression of BAG3, or a BAG3 polynucleotide or polypeptide. In preferred embodiments the cardiac disease and/or disorder is heart failure.

In other embodiments, a method of treating heart failure in a patient, comprising administering a pharmaceutical composition comprising a therapeutically effective amount of at least one agent which modulates, expression of BAG3, or a BAG3 polynucleotide or polypeptide.

In other embodiments, a method of preventing or treating a cardiac disease or disorder in a subject, comprising administering a pharmaceutical composition comprising a therapeutically effective amount of at least one agent which modulates, expression of BAG3, or a BAG3 polynucleotide or polypeptide.

In yet other embodiments, a method of preventing or treating a cardiac disease or disorder in a subject, comprising administering a pharmaceutical composition comprising a therapeutically effective amount of at least one agent which modulates, expression of BAG3, or a BAG3 polynucleotide or polypeptide and one or more therapeutic agents prescribed by the medical caregiver. In embodiments, the at least one agent which modulates, expression of BAG3, or a BAG3 polynucleotide or polypeptide and one or more therapeutic agents prescribed by the medical caregiver are administered consecutively or at the same time.

Diagnostics, Therapeutics, Kits

The compositions herein and compounds of the present invention can be utilized for diagnostics, therapeutics, and prophylaxis, and as research reagents and components of kits.

The compositions disclosed herein are generally and variously useful for treatment of a subject having a cardiac disease or disorder, for example, heart failure or dilated cardiomyopathy. We may refer to a subject, patient, or individual interchangeably. A subject is effectively treated whenever a clinically beneficial result ensues. This may mean, for example, a complete resolution of the symptoms of a disease, a decrease in the severity of the symptoms of the disease, or a slowing of the disease's progression. These methods can further include the steps of a) identifying a subject (e.g., a patient and, more specifically, a human patient) who has a cardiac disease or disorder; and b) providing to the subject with a composition comprising a nucleic acid encoding a BAG3 polypeptide. The nucleic acid encoding the BAG3 polypeptide can be inserted into a vector, for example, an AAV vector, which is administered to the subject. A subject can be identified using standard clinical tests relating to cardiac function, for example. An amount of such a composition provided to the subject that results in a complete resolution of the symptoms of the infection, a decrease in the severity of the symptoms of the infection, or a slowing of the infection's progression is considered a therapeutically effective amount. The present methods may also include a monitoring step to help optimize dosing and scheduling as well as predict outcome. In some methods of the present invention, one can first determine whether a patient has decreased levels of BAG3 and then make a determination as to whether or not to treat the patient with one or more of the compositions described herein. BAG3 levels can be assayed using, for example, an anti-BAG3 antibody, and then compared to a reference level to determine whether the patient has elevated levels of BAG3. Monitoring can also be used to rapidly distinguish responsive patients from nonresponsive patients.

Cardiovascular disorders amenable to the therapeutic, and/or prognostic methods of the invention can be disorders that are responsive to the modulation of BAG3. While we believe we understand certain events that occur in the course of treatment, the compositions of the present invention are not limited to those that work by affecting any particular cellular mechanism. Any form of cardiovascular disorder which is associated with misregulation of BAGS is within the scope of the invention.

The methods of the invention can be expressed in terms of the preparation of a medicament. Accordingly, the invention encompasses the use of the agents and compositions described herein in the preparation of a medicament. The compounds described herein are useful in therapeutic compositions and regimens or for the manufacture of a medicament for use in treatment of diseases or conditions as described herein (e.g., a cardiovascular disorder disclosed herein).

Any composition described herein can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

The dosage required will depend on the route of administration, the nature of the formulation, the nature of the patient's illness, the patient's size, weight, surface area, age, and sex, other drugs being administered, and the judgment of the attending clinicians. Suitable dosages are in the range of 0.01-1,000 mg/kg. Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the compounds in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, a compound can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present compounds can be administered once (or twice, three times, etc.) daily, weekly, monthly, or yearly.

An effective amount of any composition provided herein can be administered to an individual in need of treatment. The term "effective" as used herein refers to any amount that induces a desired response while not inducing significant toxicity in the patient. Such an amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

Any method known to those in the art can be used to determine if a particular response is induced. Clinical methods that can assess the degree of a particular disease state can be used to determine if a response is induced. The particular methods used to evaluate a response will depend upon the nature of the patient's disorder, the patient's age, and sex, other drugs being administered, and the judgment of the attending clinician.

Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks. The compositions may also be administered with another standard therapeutic agent for treatment of cardiovascular disease.

In another preferred embodiment, the agents modulate the expression of Bcl-2 associated anthanogene-3 (BAG3) in patients suffering from or at risk of developing diseases or disorders associated with molecules or pathways associated with BAG3. Examples of such diseases or disorders associated comprise: cardiac diseases or disorders, skeletal muscle diseases or disorders, multiple sclerosis, senile plaques, cerebral amyloid angiopathy, atherosclerosis, glioblastoma, amyloid deposition, neurodegenerative diseases, neurofibrillary tangles, dementia, choriocarcinoma, astrocytoma, amyloidosis, hyperlipidemia, neurodegeneration, neoplastic transformation, prostate cancer, atherosclerotic plaque, obstruction, AIDS, metastasis, myocardial infarction, pulmonary fibrosis, necrosis, shock, melanoma, colorectal carcinoma, genetic susceptibility, psoriasis, cancer, inflammation, glioma, carcinoma, breast cancer, neuropathology, tumors, prostate carcinoma, vascular diseases, cell damage, brain tumors, Non-small cell lung carcinomas (NSCLCs), hypercholesterolemia. Examples of skeletal muscles diseases include, primary (genetic) diseases of muscle (e.g., muscular dystrophies and congenital myopathies, metabolic myopathies); acquired diseases (e.g. myositis, toxic myopathy); secondary diseases of muscle (e.g. neurogenic atrophy, atrophy from chronic pulmonary, heart, kidney disease, HIV/AIDs, cancer, sarcopenia and the like.

Kits:

The present invention further provides systems and kits (e.g., commercial therapeutic, diagnostic, or research products, reaction mixtures, etc.) that contain one or more or all components sufficient, necessary, or useful to practice any of the methods described herein. These systems and kits may include buffers, detection/imaging components, positive/negative control reagents, instructions, software, hardware, packaging, or other desired components.

The kits provide useful tools for screening test compounds capable of modulating the effects of a compound on a target molecule. The kits can be packaged in any suitable manner to aid research, clinical, and testing labs, typically with the various parts, in a suitable container along with instructions for use.

In certain embodiments, the kits may further comprise lipids and/or solvents. In certain embodiments, the kits may further comprise buffers and reagents needed for the procedure, and instructions for carrying out the assay. In certain embodiments, the kits may further comprise, where necessary, agents for reducing the background interference in a test, positive and negative control reagents, apparatus for conducting a test, and the like.

Also provided are kits for determining whether a subject has a mutation in a BAG3 polypeptide, for example, the 10 base pair deletion disclosed herein, to diagnose patients having cardiovascular disease or a predisposition to developing cardiovascular disease. The kits can also be utilized to monitor the efficiency of agents used for treatment of cardiovascular disease.

Administration of Compositions

The agents identified by the methods embodied herein can be formulated and compositions of the present invention may be administered in conjunction with one or more additional active ingredients, pharmaceutical compositions, or other compounds. The therapeutic agents of the present invention may be administered to an animal, preferably a mammal, most preferably a human.

In some embodiments, a pharmaceutical composition comprises a therapeutically effective amount of at least one agent which modulates, expression of BAG3, or a BAG3 polynucleotide or polypeptide is administered as part of the treatment.

In some embodiments, a pharmaceutical composition comprises a therapeutically effective amount of at least one agent which modulates, expression of BAG3, or a BAG3 polynucleotide or polypeptide and one or more therapeutic agents prescribed by the medical caregiver.

In other embodiments, a pharmaceutical composition comprises at least one or more candidate therapeutic agents embodied herein.

The pharmaceutical formulations may be for administration by oral (solid or liquid), parenteral (intramuscular, intraperitoneal, intravenous (IV) or subcutaneous injection), intracardial, transdermal (either passively or using ionophoresis or electroporation), transmucosal and systemic (nasal, vaginal, rectal, or sublingual), or inhalation routes of administration, or using bioerodible inserts and can be formulated in dosage forms appropriate for each route of administration.

The agents may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions of the invention may be administered to animals by any conventional technique. The compositions may be administered directly to a target site by, for example, surgical delivery to an internal or external target site, or by catheter to a site accessible by a blood vessel. Other methods of delivery, e.g., liposomal delivery or diffusion from a device impregnated with the composition, are known in the art. The compositions may be administered in a single bolus, multiple injections, or by continuous infusion (e.g., intravenously). For parenteral administration, the compositions are preferably formulated in a sterilized pyrogen-free form.

The compounds identified by this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to increase BAGS expression. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect. Prodrugs of compounds of the present invention may be prepared by any suitable method.

No unacceptable toxicological effects are expected when compounds, derivatives, salts, compositions etc., of the present invention are administered in accordance with the present invention. The compounds of this invention, which may have good bioavailability, may be tested in one of several biological assays to determine the concentration of a compound which is required to have a given pharmacological effect.

In another preferred embodiment, there is provided a pharmaceutical or veterinary composition comprising one or more identified compounds and a pharmaceutically or veterinarily acceptable carrier. Other active materials may also be present, as may be considered appropriate or advisable for the disease or condition being treated or prevented.

The carrier, or, if more than one be present, each of the carriers, must be acceptable in the sense of being compatible with the other ingredients of the formulation and not deleterious to the recipient.

The compounds identified by the methods herein would be suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference. Furthermore, one may administer the drug in a targeted drug delivery system, for example, in a liposome coated with a tissue-specific antibody. The liposomes will be targeted to and taken up selectively by the organ.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product.

The compound identified using these methods can be formulated according to known methods to prepare pharmaceutically useful compositions, whereby the compound is combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™. (ICI Americas Inc., Bridgewater, N.J.), PLURONICS™. (BASF Corporation, Mount Olive, N.J.) or PEG.

The formulations to be used for in vivo administration must be sterile and pyrogen free. This is readily accomplished by filtration through sterile filtration membranes, prior to or following lyophilization and reconstitution.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

Formulations for oral administration in the present invention may be presented as: discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavoring agents such as peppermint, oil of wintergreen, cherry flavoring and the like can also be used. It may be desirable to add a coloring agent to make the dosage form readily identifiable. Tablets may also be coated by methods well known in the art.

A tablet may be made by compression or molding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavored base, usually sucrose and acacia or tragacanth; pastilles comprising the active agent in an inert base such as gelatin and glycerin, or sucrose and acacia; and mouthwashes comprising the active agent in a suitable liquid carrier.

Parenteral formulations will generally be sterile.

Dose: An effective dose of a composition of the presently disclosed subject matter is administered to a subject in need thereof. A "therapeutically effective amount" or a "therapeutic amount" is an amount of a therapeutic composition sufficient to produce a measurable response (e.g., a biologically or clinically relevant response in a subject being treated). The response can be measured in many ways, as discussed above, e.g. cytokine profiles, cell types, cell surface molecules, etc. Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. The potency of a composition can vary, and therefore a "treatment effective amount" can vary. However, using the assay methods described herein, one skilled in the art can readily assess the potency and efficacy of a candidate compound of the presently disclosed subject matter and adjust the therapeutic regimen accordingly.

The invention has been described in detail with reference to preferred embodiments thereof. However, it will be appreciated that those skilled in the art, upon consideration of this disclosure, may make modifications and improvements within the spirit and scope of the invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

EXAMPLES

While various embodiments of the present invention have been described above, it should be understood that they have been presented by way of example only, and not limitation. The following non-limiting examples are illustrative of the invention.

Example 1: Changes in BAG3 Protein Levels are Associated with Both Familial and Non-Familial Dilated Cardiomyopathy Mutations in Bcl-2 associated anthanogene-3 (BAG3), a 575 amino acid anti-apoptotic protein that serves as a co-chaperone of the heat shock proteins (HSPs), has been associated with FDC (Selcen D, et al., *Annals of Neurology*. 2009; 65:83-89; Odgerel Z, et al., *Neuromuscular disorders: NMD*. 2010; 20:438-442; Lee H C, et al., *Clinical Genetics*. 2012; 81:394-398). For example, Norton et al. recently identified a deletion of BAG3 exon 4 as a rare variant causative of FDC in a family without neuropathy or peripheral muscle weakness (Norton N, et al., *American Journal of Human Genetics*. 2011; 88:273-282). Subsequent sequencing of BAG3 in subjects diagnosed with IDC identified four additional mutations that segregated with all relatives affected by the disease. A genome-wide association study conducted in patients with HF secondary to IDC implicated a non-synonymous single nucleotide polymorphism (SNP) (c.757T>C, [p. Cys151Arg]) located within the BAG3 gene as contributing to sporadic dilated cardiomyopathy (Villard E, et al., *European Heart Journal*. 2011; 32:1065-1076).

In the present study, a novel BAG3 mutation was identified in a family with adult-onset FDC. Furthermore, it is reported herein, for the first time, that BAG3 protein levels are significantly decreased in unrelated patients with non-familial IDC evidencing that altered levels of BAG3 protein may participate in the progression of HF.

Materials and Methods

Materials: A family with adult-onset familial dilated cardiomyopathy was identified. After obtaining informed consent, participating family members underwent a physical examination by a heart failure cardiologist and blood was collected for subsequent DNA analysis. DNA was extracted using a DNA extraction kit (Qiagen, Valencia Calif.) and stored at −70° C. Whenever possible, electrocardiograms were obtained from affected family members who had not undergone heart transplantation. Family members who had not had a recent echocardiogram underwent a transthoracic echocardiogram using a SonoHeart Elite (SonoSite Inc, Bothell, Wash., USA) portable echocardiographic system. Medical records were obtained from one individual who had died. Affection status was determined on the basis of consensus guidelines (Mestroni L, et al., *European Heart Journal.* 1999; 20:93-102). Participating family members provided written informed consent prior to evaluation and the protocols were approved by the Internal Review Boards of Thomas Jefferson University and of the University of Colorado.

Methods:

Human heart tissue was obtained from 9 subjects unrelated to the study family with end-stage heart failure undergoing heart transplant at Temple University Hospital (6 male, 3 female, mean age 47.6±5.7 years), from one affected family member at the time of heart transplantation at the University of Colorado and from 7 organ donors (1 male, 6 female, mean age 59.3±3.7 years) whose hearts were unsuitable for donation owing to blood type, age or size incompatibility. All of the patients undergoing transplantation had severe left ventricular dysfunction and cardiac dilation with a mean left ventricular ejection fraction (LVEF) of 12.8±1.4%. Two of the transplant recipients had HF secondary to ischemic cardiomyopathy and the remainder had non-ischemic IDC. Four of the transplant recipients were receiving dobutamine alone, 5 were receiving milrinone alone and one was receiving both milrinone and dobutamine at the time of the transplantation. Echocardiography was performed on all of the organ donors prior to organ donation and all had normal left ventricular function by echocardiography with a mean LVEF of 57.5±1.6%. Tissue aliquots were removed from the left ventricular free wall, rapidly frozen in liquid nitrogen and stored at −70° C. as described previously (Bristow M R, et al., *The Journal of Clinical Investigation.* 1993; 92:2737-2745). The Institutional Review Boards of the University of Colorado and Temple University approved the tissue study and consent was obtained for all subjects.

Exome Sequencing and Bioinformatics:

DNA from 5 affected family members and 1 unaffected family member was selected for exome sequencing with a target depth of >100×. Exome enrichment was performed using the Agilent SureSelect Human Exon 51 Mb kit (Agilent, Santa Clara, Calif.). Paired-end 100 nucleotide exome sequencing was performed using an Illumina HiSeq 2000 platform (San Diego, Calif.). Sequence reads passing Illumina chastity filter, were subjected to a quality filter step, trimmed and retained if the trimmed reads for each pair exceeded 50 nucleotides. Paired reads were then mapped to the reference human genome sequence (hg19) with gSNAP (Wu T D, et al., *Bioinformatics.* 2010; 26:873-881). Sequence calls for variants (single-nucleotide polymorphisms [SNPs)] insertions and deletions [indels]) were performed using the Broad's Genome Analysis Toolkit (McKenna A, et al., *Genome Research.* 2010; 20:1297-1303).

After variant detection, the program Annotate Variation (ANNOVAR) was used to classify variants (e.g., exonic, intronic, synonymous, non-synonymous, splice variant, stop gain, stop loss, insertion, or deletion) and to cross reference all the variants across various genetic variation databases (e.g., dbSNP, 1000 genomes database, AVSIFT) to isolate rare variants (variants with mean allele frequencies of <1% not found in dbSNP, 1000 genomes database, aVSIFT) (Wang K, et al., *Nucleic Acids Research.* 2010; 38:e164). Only non-synonymous changes (SNPs and in-dels), those that cause an alternate splice site, and/or an aberrant stop codon, were considered for further analysis. For non-synonymous changes, all insertion and deletion variants were considered damaging, whereas SNP variants were cross-referenced to the dbNSFP database to determine whether the changes to the protein structure would be considered tolerable or damaging using four algorithms (Sorting Intolerant From Tolerant (SIFT), PolyPhen2, likelihood ratio test [LRT], or MutationTaster) (Liu X, et al., *Human Mutation.* 2011; 32:894-899). Putative mutations identified were confirmed with traditional Sanger sequencing in both affected and unaffected family members (primers and conditions available upon request).

Western Blot Analysis of Human Heart Tissue:

Frozen tissue was homogenized in 40 mM Tris buffer, pH 7.5 containing 150 mM NaCl, 1% NP40, 1 mM DTT, and 1 mM EDTA. The sample was then centrifuged at 10,000×g at 4° C. for 30 min and the supernatant was collected and re-suspended in 350 uM Tris buffer, pH 6.8 containing 25% beta-mercaptoethanol, 30% glycerol, 10% SDS, and 2% bromophenol blue. The protein concentration was measured using the method of Bradford and the samples were stored at −80° C. Equal amounts of protein (10 µg) were fractionated by SDS-polyacrylamide gel electrophoresis and transferred onto nitrocellulose membrane. Membranes were blocked in 10% nonfat dry milk/tris-buffered saline (pH 7.6) plus 0.1% Tween-20 (TBS-T) for 1 h and then incubated with polyclonal BAG3 antibody (Proteintech, Chicago, Ill.) in 5% nonfat dry milk with PBST for 2 hrs. Membranes were then incubated with goat-anti-rabbit 800 and goat-anti-mouse secondary antibody for 1 hr and scanned on a LI-COR Odyssey imaging system (Lincoln Nebr.). All Western blot procedures were carried out at room temperature. BAG3 signal intensity was normalized to GAPDH.

Results

Family History:

The proband (FIG. 1, III-5) was a 65 year-old woman of Eastern European ancestry who was referred in June 2003 to the heart failure clinic at Thomas Jefferson University because of a family history of HF. She had first been noted to have a dilated cardiomyopathy at 45 years of age. She was largely asymptomatic while receiving a diuretic, a β-adrenergic receptor antagonist (β-blocker) and an angiotensin converting enzyme (ACE) inhibitor. Her vital signs were within normal limits and her physical examination was notable only for a soft S3 heart sound. She had no peripheral muscle weakness and her neurologic examination was unremarkable. Her electrocardiogram revealed normal sinus rhythm with mild LV hypertrophy and non-specific ST-T wave changes. Her left ventricular ejection fraction was 20% by echocardiography. As seen in FIG. 1 and Table 1, the proband had two female siblings, one of whom (III-7) was asymptomatic with a normal physical examination; however, her ejection fraction by echocardiography was 44%. A second sister (III-9) was phenotypically normal and had a normal echocardiogram.

The proband had three children. A son underwent cardiac transplantation at the age of 20 secondary to IDC (IV-5), a second son was diagnosed with idiopathic dilated cardiomyopathy at the age of 20 but remained asymptomatic at age 32 despite an ejection fraction of 33% (IV-4). A daughter had no cardiac symptoms; however, her left ventricular ejection fraction by echocardiography was 48% and she had mild dilatation of the left ventricle and the aortic root without obvious aortic valve disease. (IV-6) Her echocardiogram met the criteria for diagnosis of a dilated cardiomyopathy. Her electrocardiogram was normal. Neurologic function was normal in all three children. The proband's affected sister (III-7) had one daughter who died of progressive heart failure secondary to IDC at the age of 22. (IV-7): two other children had normal echocardiograms. A cousin underwent cardiac transplantation because of IDC at 42 years of age after diagnosis at the age of 40 (III-1) and one of his sons also underwent cardiac transplantation for IDC at the University of Colorado at the age of 30 (IV-1). Healthy subjects were defined as "non-affected" if they had reached the age of 40 without symptoms and had a normal echocardiogram that did not meet the criteria for diagnosis of a cardiomyopathy. Ten-year follow-up of all participants demonstrated that functional capacity had remained stable in all family members.

Genetic Analysis:

As seen in FIG. 1, the pedigree and clinical data were compatible with autosomal dominant adult-onset familial IDC. Exome sequencing of the DNA from 5 affected (III-5, 7: IV-1, 4, 5) and 1 unaffected (III-9) family members had an average of 11.8±0.96 Gb of past-filter sequence reads per sample. After bioinformatics filtering a 10-nucleotide deletion in the coding portion of exon 4 of BAG3 (Ch10:del 121436332_12143641: del. 1266_1275 [NM 004281]) was noted to be present in all tested affected subjects and absent in the one healthy sister of the proband (III-9) (FIG. 2). Additional family members were tested for the BAG3 deletion by Sanger sequencing confirming appropriate co-segregation of the deletion with the phenotype among affected (III-1, 5, 7 and IV-1, 4, 5, 6) and unaffected (III-9 and IV-8, 9, 10, 11, 12) individuals. This deletion was not found in existing databases and introduces a frame shift and premature stop codon after 13 amino acids that predicts truncation of BAG3 at the carboxy terminal end by 140 amino acids. Thus, the abnormal BAG3 protein is predicted to have 435 amino acids instead of 575 amino acids. In addition, the amino acid sequence distal to the deletion (K P S W R R Y R G W S R L) (SEQ ID NO:8) is predicted to be different from that found in the normal protein. Only one additional variant was found by exome sequencing and after bioinformatics filtering. The variant (rs8192669), found in the IKZF5 gene did not segregate according to the IDC phenotype in other family members. An analysis of 52 genes previously associated with monogenic IDC for rare variants (≤1%) identified only non-synonymous mutations in TTN, GATAD1, MYPN, ANKRD1 and RBM20: none of these variants segregated with the disease phenotype.

Figure 3B:
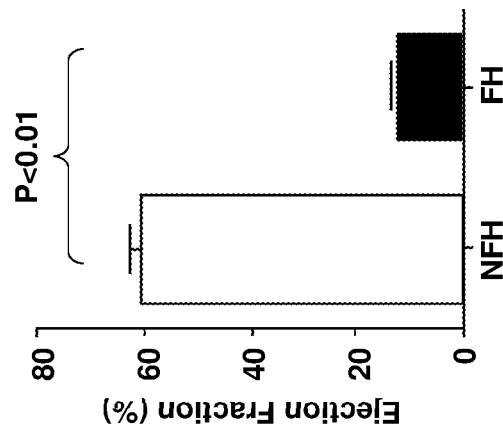
FIGS. 3A-3B show the low level expression of BAG3 in patients with heart failure. A representative Western blot of BAG3 and GAPDH levels in non-failing (NF) and failing (F) human heart is shown. The graph shows the quantification of BAG3 protein levels in non-failing and failing human heart. Values are normalized to the level of GAPDH in order to account for variations in protein loading. Horizontal lines represent mean and standard error of the mean. Statistical analysis was performed using unpaired t-test with Welch's correction for unequal variance.
Figure 3A:
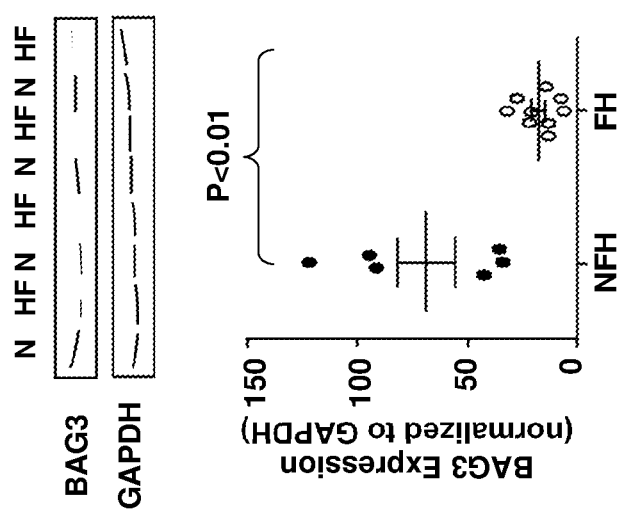
Figure 4:
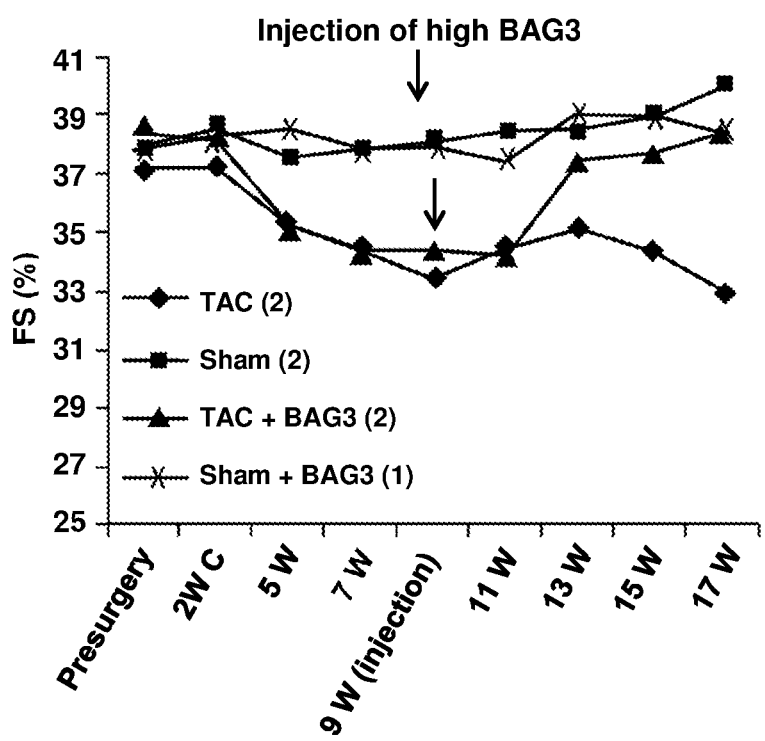
FIG. 4 shows the measurement of ejection fraction in wild type sham operated mice, wild type mice that have been injected with the AAV9-BAG3 construct, mice that have undergone aortic banding (and developed heart failure) and mice that have been banded and in heart failure but were injected with AAV9-BAG3. As can be seen, the BAG3 injection normalized LV function temporally related to the expression of the BAG3 protein (approximately 5 to 6 weeks after injection).
Figure 5:
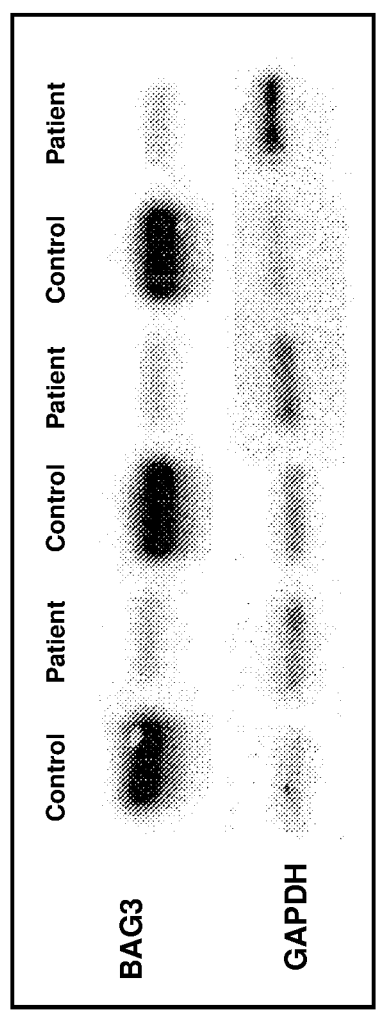
FIG. 5 is a Western Blot showing BAG3 levels in patients. Three lanes of "control" and three lanes of "patient" are shown. This is patient IV-1—who is an affected. The "control" lanes are from a non-failing human heart—i.e. Normal human heart—that was obtained at the time of tissue harvest but could not be used for transplant because of size or tissue type incompatibility with available recipients. All of the lanes labeled "patient" were from the same patient—IV-1. These were obtained from pieces of his heart that were explanted at the time he underwent a heart transplant. The results show that the decrease in BAG3 levels are comparable to the decrease that was seen in the patients with non-familial heart failure.

BAG 3 Expression in Failing Human Heart:

In order to determine whether the BAG3 deletion (BAG3 del. NM_004281) found in this patient cohort resulted in a decrease in the levels of BAG3 protein, Western blot analysis was performed on cardiac muscle obtained from one affected family member (IV-1) who underwent cardiac transplantation. The level of BAG3 protein in subject IV-1 was less than half that seen in heart tissue obtained from organ donors whose heart could not be utilized for transplantation. As seen in FIGS. 3A and 3B, BAG3 levels in failing human heart from patients with end stage heart failure without known BAG3 mutations were significantly (p=0.0002) less than that found in non-failing control hearts. Thus it appears that decreased levels of BAG3 protein can be found both in individuals with a BAG3 mutation as well as in end-stage failing human heart.

DISCUSSION

It is being increasingly recognized that genetic mutations can account for as many as a third of cases of IDC. Indeed, investigators have begun to refer to these cases as familial dilated cardiomyopathy (FDC). Inheritance can occur in a variety of manners with the most common pattern of inheritance being autosomal dominant. Mutations are most commonly found in genes encoding the sarcomere leading to cardiac dysfunction, disintegration of the myofiber structure and accumulation of degraded material in autophagic granules. Here, it is reported that a 10 bp deletion in the gene encoding the sarcomeric protein BAG3 segregates completely with affected individuals in a family with an autosomal dominant pattern of FDC. It is also report for the first time that BAG3 protein is substantially reduced in the hearts of unrelated patients who are undergoing heart transplantation when compared with normal hearts from transplant recipients.

BAG3 is a 575 amino acid anti-apoptotic protein that is constitutively expressed in the heart and serves as a co-chaperone of the heat shock proteins (HSPs). BAG3 binds to HSPs and regulates their ability to chaperone cytoskeletal proteins including desmin and also participate in degradation of cellular proteins through either the proteasome or autophagy pathways. BAG3 also protects cells from apoptotic death and inhibits myofibrillar degeneration in response to mechanical stress. Knockdown of BAG3 in zebrafish or in neonatal cardiomyoctes or homozygous disruption of BAG3 in mice leads to cardiac dysfunction and BAG3 levels are decreased in the skeletal muscle of spontaneously hypertensive rats.

The results of the present study in a large family with FDC are consistent with earlier reports that demonstrated an association between mutations in BAG3 and the development of muscle pathology. Mutations in BAG3 were first shown to cause abnormal muscle function in two families with childhood-onset muscular dystrophy (Selcen D, et al., *Annals of Neurology.* 2009; 65:83-89; Odgerel Z, et al., Neuromuscular Disorders: NMD. 2010; 20:438-442) and the phenotype of IDC, diffuse myocardial fibrosis and sudden death was linked with markers in the chromosome 10q25-26 region which includes the BAG3 locus. More recent studies have demonstrated a causative relationship between BAG3 mutations and the development of FDC without peripheral muscle weakness or neurologic findings (Norton N, et al., *American Journal of Human Genetics.* 2011; 88:273-282; Villard E, et al., *European Heart Journal.* 2011; 32:1065-1076; Arimura T, et al., *Human Mutation.* 2011; 32:1481-1491).

As seen with genetic variants in other sarcomeric genes, there was substantial genetic heterogeneity within this large family. For example, one of the proband's sons had an early onset of severe disease requiring transplantation whereas a sibling with moderate disease and a middle-aged daughter with very mild disease remain asymptomatic for over a decade. Indeed, the cardiac dysfunction in the proband's daughter would have gone unrecognized had it not been for careful phenotyping as part of this study. Identification of the causative mutation in this family provides an opportunity for guideline-driven genetic testing and counseling of family members and early identification of affected individuals. The finding that use of an angiotensin converting enzyme inhibitor improved survival in a small group of patients with Duchenne muscular dystrophy suggests that early therapy in families with mutations in sarcomere genes might be beneficial; however, additional studies will be required to define the best treatment strategies.

It is reported herein, for the first time that the level of BAG3 protein is significantly reduced in the hearts of unrelated patients with end-stage HF who are undergoing heart transplant and who have no family history of heart muscle disease. This finding is interesting as it evidences that while mutations in BAG3 can be causative of disease in FDC, changes in levels of BAG3 protein may participate in the progression of disease in patients with non-familial forms of IDC. Nonetheless, these results evidence that BAG3 protein might be a new target for therapeutic intervention in HF.

Example 2: Changes in BAG3 Protein Levels in Failing Murine Hearts

Figure 6B:
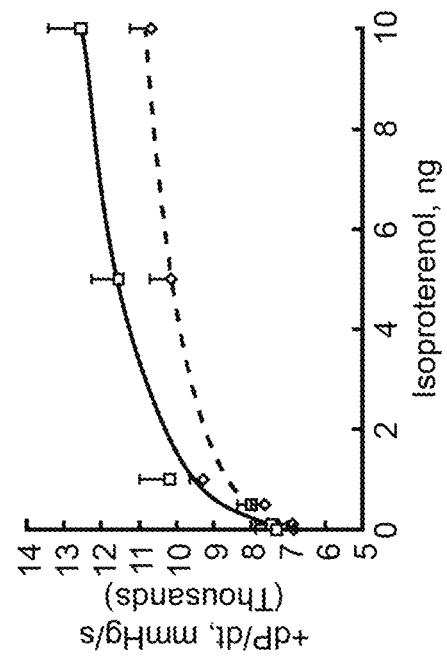
FIGS. 6A-6D show BAG3 levels in failing murine hearts.
Figure 6A:
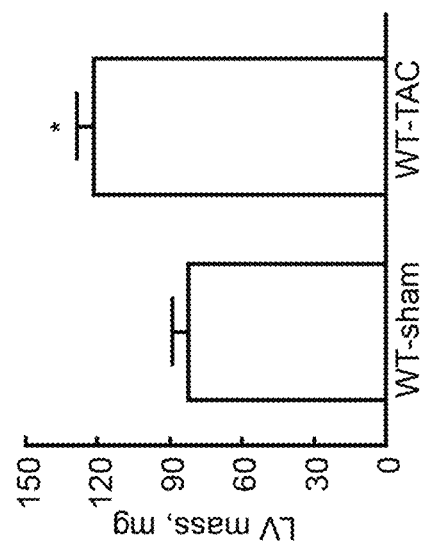
Figures 6C, 6D:
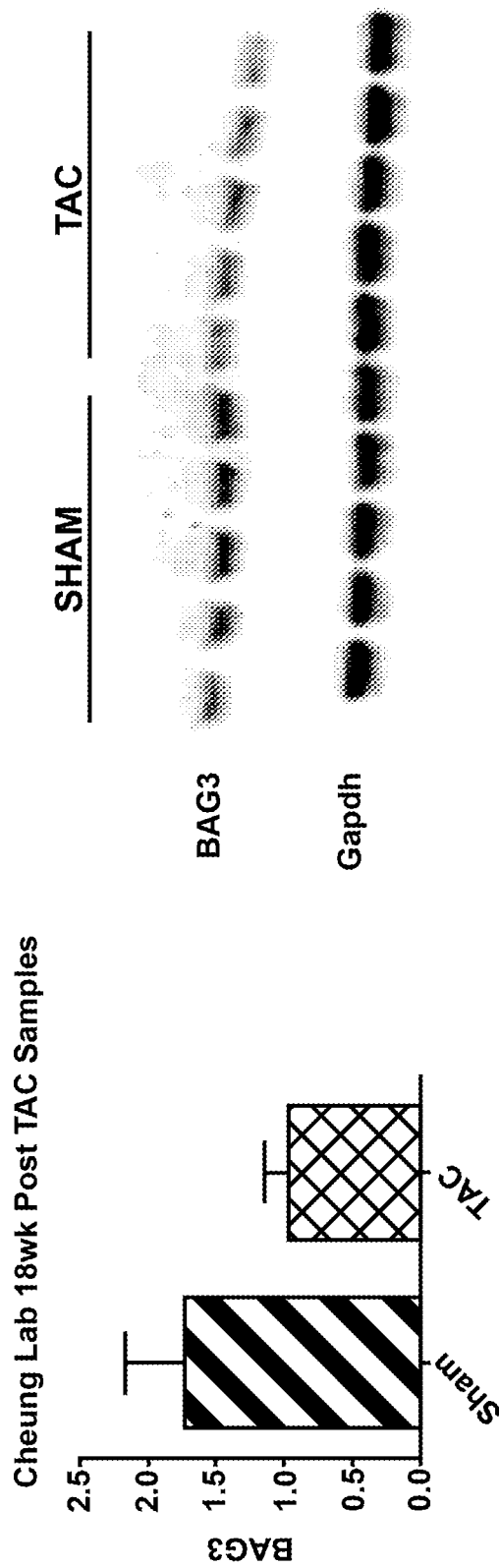

Wild type c57BL/6 mice underwent trans-aortic banding (TAC) as described in Tilley et al. (*Circulation* 2014, Nov. 11; 130(20):1800-11). Eighteen weeks after TAC, left ventricular contractility was measured using a conductance catheter inserted into the left ventricle through a carotid approach as described previously. Contractility was measured during intravenous infusion of increasing doses of catecholamine. (FIG. 6B) Heart weight to body weight ratios were calculated after sacrifice. (FIG. 6A). Hearts were then frozen for subsequent measurement of BAG3 levels. Myocardial proteins were extracted as described in Example 1, separated by gel electrophoresis and probed with a murine BAG3 antibody. As shown in FIG. 6C, there was a significant decrease in BAG3 levels by Western blotting in TAC mice when compared with sham-operated controls. A representative Western blot is shown in FIG. 6D.

Figure 7A:
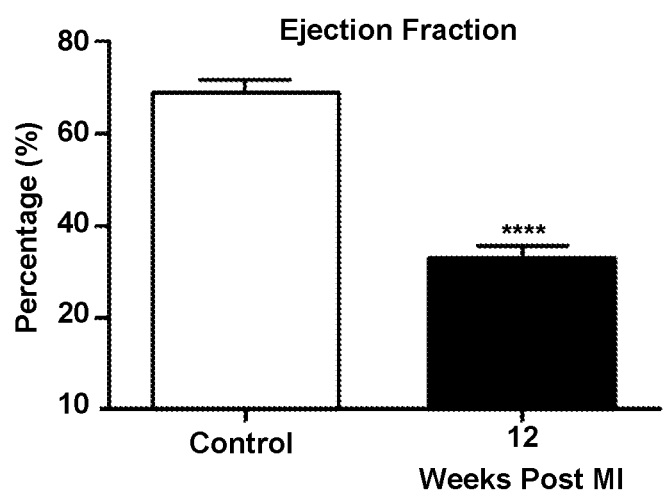
FIGS. 7A-7F show hemodynamic indices and BAG3 levels in porcine hearts following balloon occlusion.
Figure 7B:
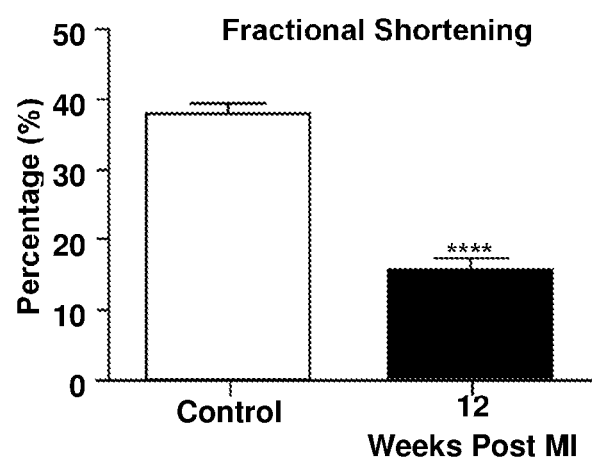
Figure 7C:
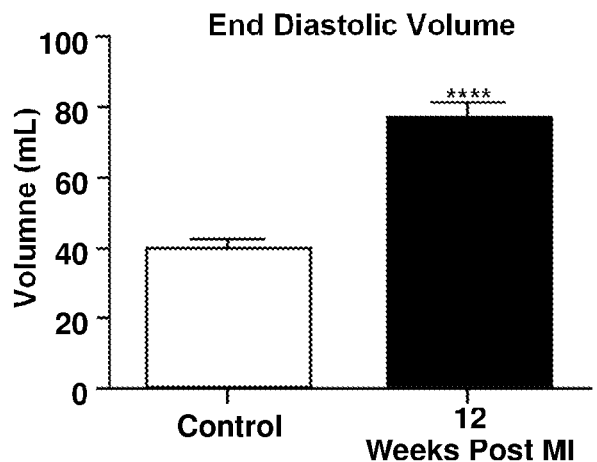
Figure 7D:
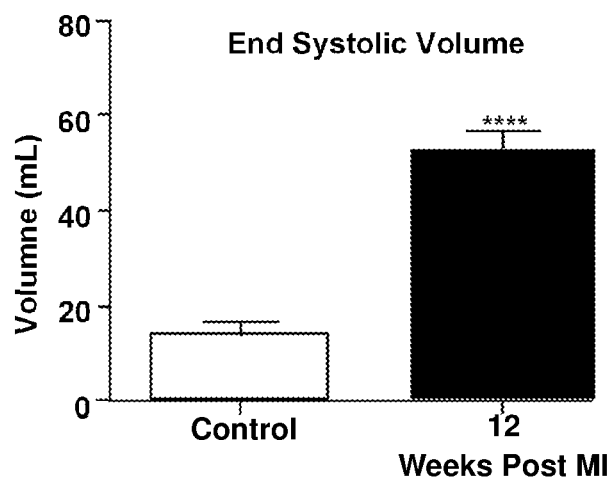
Figure 7F:
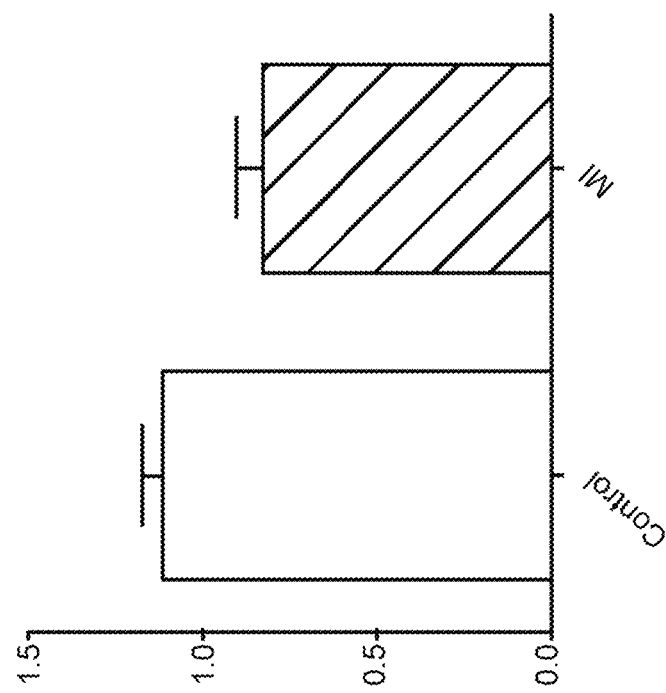
Figure 7E:
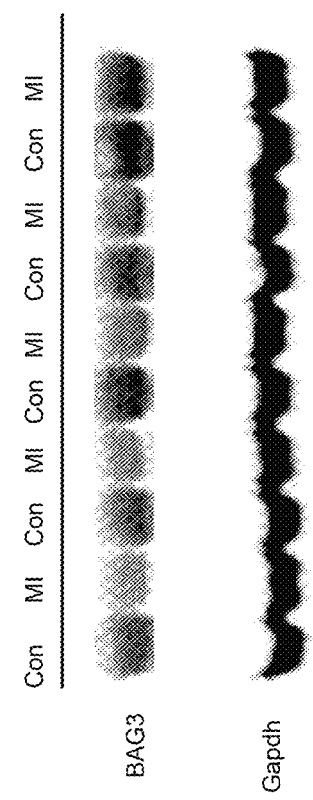

Example 3: Changes in BAG3 Protein Levels in Porcine Hearts Following Balloon Occlusion Hemodynamic indices and BAG3 levels were measured in non-infarcted left ventricular myocardium from a pig 4 weeks after balloon occlusion of the left anterior descending coronary artery. As shown in 7A, 7B, 7C, and 7D, ejection fraction, fractional shortening, end-diastolic volume, and end systolic volume, respectively, were significantly altered following balloon occlusion. As shown graphically in FIG. 7E, and in the Western blot in FIG. 7F, BAG3 levels were reduced in porcine hearts following balloon occlusion.

TABLE 1

Phenotype of study subjects with and without a 10-nucleotide deletion in the BAG3 gene.

| Subject | Age Eval/Onset/Death or Transpl | Gender | EF(%) | ECG | Mutation | Comment |
|---|---|---|---|---|---|---|
| II-1 | na/na/70+ | M | | | | Died late 70's, hx of HF |
| II-3 | na/na/80 | F | | | | Hx of HBP and CVA |
| II-4 | na/na/29 | M | | | | motor vehicle accident |
| III-1 | 62/40/42 | M | | | Yes | transplant at 42 |
| III-5 | 65/45/na | F | 20 | NS-ST-T changes | Yes | |
| III-7 | 67/47/na | F | 44 | nl | Yes | asymptomatic |
| III-9 | 68/na/na | F | 58 | nl | No | |
| IV-1 | 30/30/30 | M | | | Yes | transplant at 30 |
| IV-4 | 39/20/na | M | 33 | sinus brady, IVCD | Yes | asymptomatic |
| IV-5 | 35/20/20 | M | | | Yes | transplant at 20 |
| IV-6 | 34/34/na | F | 48 | nl | Yes | mild aortic root dilat, LVDD 5.8 |
| IV-7 | na/18/22 | F | | | | died-worsening HF |
| IV-8 | 38 | F | | nl | No | |
| IV-9 | 42 | M | | nl | No | |
| IV-10 | 41 | F | | nl | No | |
| IV-11 | 44 | M | | nl | No | |
| IV-12 | 45 | M | | nl | No | |

What is claimed is:

1. A method of treating a human patient suffering from heart failure with reduced ejection fraction, wherein the human patient expresses a decreased level of BCL2-associated athanogene 3 (BAG3) polynucleotide or polypeptide, comprising:
   administering to the human patient's heart a therapeutically effective amount of an isolated BAG3 gene, BAG3 polynucleotide, BAG3 protein, BAG3 polypeptide or an expression vector comprising a BAG3 polynucleotide or cDNA sequence thereof to increase expression or amount of BAG3 polypeptides or proteins in the human patient's heart.

2. The method of claim 1, wherein the human patient has a mutation in their BAG3 polynucleotide or polypeptide.

3. The method of claim 1, wherein the expression vector comprises a viral vector, eukaryotic or prokaryotic plasmid, or yeast vector.

4. The method of claim 3, wherein the viral vector comprises an adeno-associated virus vector (AAV), adenovirus vector, coxsackie virus vector, a cytomegalovirus vector, a lentivirus or retroviral vector.

5. The method of claim 4, wherein the adeno-associated virus comprises: serotype 1 (AAV1), serotype 2 (AAV2), serotype 3 (AAV3), serotype 4 (AAV4), serotype 5 (AAV5), serotype 6 (AAV6), serotype 7 (AAV7), serotype 8 (AAV8), or serotype 9 (AAV9) capsid protein.

6. The method of claim 1, wherein the human patient suffers from familial dilated cardiomyopathy.

7. The method of claim 1, wherein the human patient suffers from non-familial dilated cardiomyopathy.

8. The method of claim 1, wherein the BAG3 gene, BAG3 polynucleotide, BAG3, protein, BAG3 polypeptide or an expression vector comprising a BAG3 polynucleotide or cDNA sequence thereof is comprised in a pharmaceutical composition.

9. The method of claim 1, wherein the expression vector comprising a BAG3 polynucleotide or cDNA sequence thereof further comprises a cardiac specific promoter.

10. The method of claim 9, wherein the expression vector comprising the BAG3 polynucleotide or cDNA sequence that further comprises a cardiac specific promoter is flanked by one or more inverted terminal repeats (ITRs).

11. The method of claim 10, wherein the one or more ITRs comprise AAV2 ITRs.

12. The method of claim 1, wherein the expression vector comprising a BAG3 polynucleotide or cDNA sequence thereof further comprises a CMV promoter.

13. The method of claim 12, wherein the expression vector comprising the BAG3 polynucleotide or cDNA sequence that further comprises a CMV promoter is flanked by one or more inverted terminal repeats (ITRs).

14. The method of claim 13, wherein the one or more ITRs comprise AAV2 ITRs.

15. The method of claim 1, wherein the human patient suffers from ischemic heart disease.

16. The method of claim 1, wherein the human patient suffers from non-ischemic cardiomyopathy.

17. The method of claim 1, wherein the BAG3 gene, BAG3 polynucleotide, BAG3 protein, BAG3 polypeptide or an expression vector comprising a BAG3 polynucleotide or cDNA sequence thereof is intravenously administered.

* * * * *

SEQUENCE LISTING

<160> NUMBER OF SEQ ID NOS: 51

<210> SEQ ID NO 1
<211> LENGTH: 575
<212> TYPE: PRT
<213> ORGANISM: Homo sapiens

<400> SEQUENCE: 1

Met Ser Ala Ala Thr His Ser Pro Met Met Gln Val Ala Ser Gly Asn
1               5                   10                  15

Gly Asp Arg Asp Pro Leu Pro Pro Gly Trp Glu Ile Lys Ile Asp Pro
            20                  25                  30

Gln Thr Gly Trp Pro Phe Phe Val Asp His Asn Ser Arg Thr Thr Thr
        35                  40                  45

-continued

Trp Asn Asp Pro Arg Val Pro Ser Glu Gly Pro Lys Glu Thr Pro Ser
    50                  55                  60

Ser Ala Asn Gly Pro Ser Arg Glu Gly Ser Arg Leu Pro Ala Arg
65                  70                  75                  80

Glu Gly His Pro Val Tyr Pro Gln Leu Arg Pro Gly Tyr Ile Pro Ile
                    85                  90                  95

Pro Val Leu His Glu Gly Ala Glu Asn Arg Gln Val His Pro Phe His
                100                 105                 110

Val Tyr Pro Gln Pro Gly Met Gln Arg Phe Arg Thr Glu Ala Ala Ala
            115                 120                 125

Ala Ala Pro Gln Arg Ser Gln Ser Pro Leu Arg Gly Met Pro Glu Thr
130                 135                 140

Thr Gln Pro Asp Lys Gln Cys Gly Gln Val Ala Ala Ala Ala Ala Ala
145                 150                 155                 160

Gln Pro Pro Ala Ser His Gly Pro Glu Arg Ser Gln Ser Pro Ala Ala
                165                 170                 175

Ser Asp Cys Ser Ser Ser Ser Ser Ala Ser Leu Pro Ser Ser Gly
            180                 185                 190

Arg Ser Ser Leu Gly Ser His Gln Leu Pro Arg Gly Tyr Ile Ser Ile
        195                 200                 205

Pro Val Ile His Glu Gln Asn Val Thr Arg Pro Ala Ala Gln Pro Ser
    210                 215                 220

Phe His Gln Ala Gln Lys Thr His Tyr Pro Ala Gln Gln Gly Glu Tyr
225                 230                 235                 240

Gln Thr His Gln Pro Val Tyr His Lys Ile Gln Gly Asp Asp Trp Glu
                245                 250                 255

Pro Arg Pro Leu Arg Ala Ala Ser Pro Phe Arg Ser Ser Val Gln Gly
            260                 265                 270

Ala Ser Ser Arg Glu Gly Ser Pro Ala Arg Ser Ser Thr Pro Leu His
        275                 280                 285

Ser Pro Ser Pro Ile Arg Val His Thr Val Val Asp Arg Pro Gln Gln
    290                 295                 300

Pro Met Thr His Arg Glu Thr Ala Pro Val Ser Gln Pro Glu Asn Lys
305                 310                 315                 320

Pro Glu Ser Lys Pro Gly Pro Val Gly Pro Glu Leu Pro Pro Gly His
                325                 330                 335

Ile Pro Ile Gln Val Ile Arg Lys Glu Val Asp Ser Lys Pro Val Ser
            340                 345                 350

Gln Lys Pro Pro Pro Ser Glu Lys Val Glu Val Lys Val Pro Pro
        355                 360                 365

Ala Pro Val Pro Cys Pro Pro Ser Pro Gly Pro Ser Ala Val Pro
    370                 375                 380

Ser Ser Pro Lys Ser Val Ala Thr Glu Glu Arg Ala Ala Pro Ser Thr
385                 390                 395                 400

Ala Pro Ala Glu Ala Thr Pro Pro Lys Pro Gly Glu Ala Glu Ala Pro
                405                 410                 415

Pro Lys His Pro Gly Val Leu Lys Val Glu Ala Ile Leu Glu Lys Val
            420                 425                 430

Gln Gly Leu Glu Gln Ala Val Asp Asn Phe Glu Gly Lys Lys Thr Asp
        435                 440                 445

Lys Lys Tyr Leu Met Ile Glu Glu Tyr Leu Thr Lys Glu Leu Leu Ala
    450                 455                 460

Leu Asp Ser Val Asp Pro Glu Gly Arg Ala Asp Val Arg Gln Ala Arg
465                 470                 475                 480

Arg Asp Gly Val Arg Lys Val Gln Thr Ile Leu Glu Lys Leu Glu Gln
                485                 490                 495

Lys Ala Ile Asp Val Pro Gly Gln Val Gln Val Tyr Glu Leu Gln Pro
            500                 505                 510

Ser Asn Leu Glu Ala Asp Gln Pro Leu Gln Ala Ile Met Glu Met Gly
        515                 520                 525

Ala Val Ala Ala Asp Lys Gly Lys Lys Asn Ala Gly Asn Ala Glu Asp
    530                 535                 540

Pro His Thr Glu Thr Gln Gln Pro Glu Ala Thr Ala Ala Ala Thr Ser
545                 550                 555                 560

Asn Pro Ser Ser Met Thr Asp Thr Pro Gly Asn Pro Ala Ala Pro
                565                 570                 575

<210> SEQ ID NO 2
<211> LENGTH: 2608
<212> TYPE: DNA
<213> ORGANISM: Homo sapiens

<400> SEQUENCE: 2

| | | |
|---|---|---|
| gcggagctcc gcatccaacc ccgggccgcg gccaacttct ctggactgga ccagaagttt | 60 |
| ctagccggcc agttgctacc tccctttatc tcctccttcc cctctggcag cgaggaggct | 120 |
| atttccagac acttccaccc ctctctggcc acgtcacccc cgcctttaat tcataaaggt | 180 |
| gcccggcgcc ggcttcccgg acacgtcggc ggcggagagg ggccacggc ggcggcccgg | 240 |
| ccagagactc ggcgcccgga ccagcgccc cgcacccgcg cccagcggg cagaccccaa | 300 |
| cccagcatga gcgccgccac ccactcgccc atgatgcagg tggcgtccgg caacggtgac | 360 |
| cgcgaccctt tgcccccggg atgggagatc aagatcgacc cgcagaccgg ctggcccttc | 420 |
| ttcgtggacc acaacagccg caccactacg tggaacgacc cgcgcgtgcc ctctgagggc | 480 |
| cccaaggaga ctccatcctc tgccaatggc ccttcccggg agggtctag gctgccgcct | 540 |
| gctagggaag gccaccctgt gtaccccag ctccgaccag gctacattcc cattcctgtg | 600 |
| ctccatgaag gcgctgagaa ccggcaggtg caccctttcc atgtctatcc ccagcctggg | 660 |
| atgcagcgat tccgaactga ggcggcagca gcggctcctc agaggtccca gtcacctctg | 720 |
| cggggcatgc cagaaaccac tcagccagat aaacagtgtg acaggtggc agcggcggcg | 780 |
| gcagcccagc cccagcctc ccacggacct gagcggtccc agtctccagc tgcctctgac | 840 |
| tgctcatcct catcctcctc ggccagcctg ccttcctccg gcaggagcag cctgggcagt | 900 |
| caccagctcc gcggggggta catctccatt ccggtgatac acgagcagaa cgttacccgg | 960 |
| ccagcagccc agccctcctt ccaccaagcc cagaagacgc actacccagc gcagcagggg | 1020 |
| gagtaccaga cccaccagcc tgtgtaccac aagatccagg gggatgactg ggagccccgg | 1080 |
| cccctgcggg cggcatcccc gttcaggtca tctgtccagg gtgcatcgag ccgggagggc | 1140 |
| tcaccagcca ggagcagcac gccactccac tcccctcgc ccatccgtgt gcacaccgtg | 1200 |
| gtcgacaggc ctcagcagcc catgacccat cgagaaactg cacctgtttc ccagcctgaa | 1260 |
| aacaaaccag aaagtaagcc aggcccagtt ggaccagaac tccctcctgg acacatccca | 1320 |
| attcaagtga tccgcaaaga ggtggattct aaacctgttt cccagaagcc cccacctccc | 1380 |
| tctgagaagg tagaggtgaa agttccccct gctccagttc cttgtcctcc tcccagccct | 1440 |
| ggcccttctg ctgtccccctc ttcccccaag agtgtgggcta cagaagagag ggcagccccc | 1500 |

```
agcactgccc ctgcagaagc tacacctcca aaaccaggag aagccgaggc tcccccaaaa    1560
catccaggag tgctgaaagt ggaagccatc ctggagaagg tacaggggct ggagcaggct    1620
gtagacaact ttgaaggcaa aagactgac aaaaagtacc tgatgatcga agagtatttg    1680
accaaagagc tgctggccct ggattcagtg gaccccgagg acgagccga tgtgcgtcag    1740 gccaggagag acggtgtcag gaaggttcag accatcttgg aaaaacttga acagaaagcc    1800
attgatgtcc caggtcaagt ccaggtctat gaactccagc ccagcaacct tgaagcagat    1860
cagccactgc aggcaatcat ggagatgggt gccgtggcag cagacaaggg caagaaaaat    1920
gctggaaatg cagaagatcc ccacacagaa acccagcagc agaagccac agcagcagcg    1980 acttcaaacc ccagcagcat gacagacacc cctggtaacc cagcagcacc gtagcctctg    2040
ccctgtaaaa atcagactcg gaaccgatgt gtgctttagg gaattttaag ttgcatgcat    2100
ttcagagact ttaagtcagt tggttttat tagctgcttg gtatgcagta acttgggtgg    2160
aggcaaaaca ctaataaag ggctaaaaag gaaaatgatg cttttcttct atattcttac    2220
tctgtacaaa taaagaagtt gcttgttgtt tgagaagttt aaccccgttg cttgttgttc    2280
tgcagccctg tctacttggg cacccccacc acctgttagc tgtggttgtg cactgtcttt    2340
tgtagctctg gactggaggg gtagatgggg agtcaattac ccatcacata aatatgaaac    2400
atttatcaga aatgttgcca ttttaatgag atgattttct tcatctcata attaaaatac    2460
ctgactttag agagtaaa atgtgccagg agccatagga atatctgtat gttggatgac    2520
tttaatgcta cattttaaaa aagaaaata aagtaataat ataactcaaa aaaaaaaaa    2580 aaaaaaaaaa aaaaaaaaaa aaaaaaa                                       2608
```

<210> SEQ ID NO 3
<211> LENGTH: 575
<212> TYPE: PRT
<213> ORGANISM: Homo sapiens

<400> SEQUENCE: 3

Met Ser Ala Ala Thr His Ser Pro Met Met Gln Val Ala Ser Gly Asn
1               5                   10                  15

Gly Asp Arg Asp Pro Leu Pro Pro Gly Trp Glu Ile Lys Ile Asp Pro
            20                  25                  30

Gln Thr Gly Trp Pro Phe Phe Val Asp His Asn Ser Arg Thr Thr Thr
        35                  40                  45

Trp Asn Asp Pro Arg Val Pro Ser Glu Gly Pro Lys Glu Thr Pro Ser
    50                  55                  60

Ser Ala Asn Gly Pro Ser Arg Glu Gly Ser Arg Leu Pro Pro Ala Arg
65                  70                  75                  80

Glu Gly His Pro Val Tyr Pro Gln Leu Arg Pro Gly Tyr Ile Pro Ile
                85                  90                  95

Pro Val Leu His Glu Gly Ala Glu Asn Arg Gln Val His Pro Phe His
            100                 105                 110

Val Tyr Pro Gln Pro Gly Met Gln Arg Phe Arg Thr Glu Ala Ala Ala
        115                 120                 125

Ala Ala Pro Gln Arg Ser Gln Ser Pro Leu Arg Gly Met Pro Glu Thr
    130                 135                 140

Thr Gln Pro Asp Lys Gln Cys Gly Gln Val Ala Ala Ala Ala Ala
145                 150                 155                 160

Gln Pro Pro Ala Ser His Gly Pro Glu Arg Ser Gln Ser Pro Ala Ala
                165                 170                 175

```
Ser Asp Cys Ser Ser Ser Ser Ser Ala Ser Leu Pro Ser Ser Gly
            180                 185                 190

Arg Ser Ser Leu Gly Ser His Gln Leu Pro Arg Gly Tyr Ile Ser Ile
    195                 200                 205

Pro Val Ile His Glu Gln Asn Val Thr Arg Pro Ala Ala Gln Pro Ser
    210                 215                 220

Phe His Gln Ala Gln Lys Thr His Tyr Pro Ala Gln Gln Gly Glu Tyr
225                 230                 235                 240

Gln Thr His Gln Pro Val Tyr His Lys Ile Gln Gly Asp Asp Trp Glu
            245                 250                 255

Pro Arg Pro Leu Arg Ala Ala Ser Pro Phe Arg Ser Ser Val Gln Gly
            260                 265                 270

Ala Ser Ser Arg Glu Gly Ser Pro Ala Arg Ser Ser Thr Pro Leu His
            275                 280                 285

Ser Pro Ser Pro Ile Arg Val His Thr Val Val Asp Arg Pro Gln Gln
    290                 295                 300

Pro Met Thr His Arg Glu Thr Ala Pro Val Ser Gln Pro Glu Asn Lys
305                 310                 315                 320

Pro Glu Ser Lys Pro Gly Pro Val Gly Pro Glu Leu Pro Pro Gly His
            325                 330                 335

Ile Pro Ile Gln Val Ile Arg Lys Glu Val Asp Ser Lys Pro Val Ser
            340                 345                 350

Gln Lys Pro Pro Pro Ser Glu Lys Val Glu Val Lys Val Pro Pro
            355                 360                 365

Ala Pro Val Pro Cys Pro Pro Ser Pro Gly Pro Ser Ala Val Pro
            370                 375                 380

Ser Ser Pro Lys Ser Val Ala Thr Glu Glu Arg Ala Ala Pro Ser Thr
385                 390                 395                 400

Ala Pro Ala Glu Ala Thr Pro Pro Lys Pro Gly Glu Ala Glu Ala Pro
            405                 410                 415

Pro Lys His Pro Gly Val Leu Lys Val Glu Ala Ile Leu Glu Lys Val
            420                 425                 430

Gln Gly Leu Glu Gln Ala Val Asp Asn Phe Glu Gly Lys Lys Thr Asp
            435                 440                 445

Lys Lys Tyr Leu Met Ile Glu Glu Tyr Leu Thr Lys Glu Leu Leu Ala
450                 455                 460

Leu Asp Ser Val Asp Pro Glu Gly Arg Ala Asp Val Arg Gln Ala Arg
465                 470                 475                 480

Arg Asp Gly Val Arg Lys Val Gln Thr Ile Leu Glu Lys Leu Glu Gln
            485                 490                 495

Lys Ala Ile Asp Val Pro Gly Gln Val Gln Val Tyr Glu Leu Gln Pro
            500                 505                 510

Ser Asn Leu Glu Ala Asp Gln Pro Leu Gln Ala Ile Met Glu Met Gly
            515                 520                 525

Ala Val Ala Ala Asp Lys Gly Lys Lys Asn Ala Gly Asn Ala Glu Asp
            530                 535                 540

Pro His Thr Glu Thr Gln Gln Pro Glu Ala Thr Ala Ala Thr Ser
545                 550                 555                 560

Asn Pro Ser Ser Met Thr Asp Thr Pro Gly Asn Pro Ala Ala Pro
            565                 570                 575

<210> SEQ ID NO 4
<211> LENGTH: 575
<212> TYPE: PRT
```

<213> ORGANISM: Homo sapiens

<400> SEQUENCE: 4

```
Met Ser Ala Ala Thr His Ser Pro Met Met Gln Val Ala Ser Gly Asn
1               5                   10                  15

Gly Asp Arg Asp Pro Leu Pro Pro Gly Trp Glu Ile Lys Ile Asp Pro
            20                  25                  30

Gln Thr Gly Trp Pro Phe Phe Val Asp His Asn Ser Arg Thr Thr Thr
        35                  40                  45

Trp Asn Asp Pro Arg Val Pro Ser Glu Gly Pro Lys Glu Thr Pro Ser
    50                  55                  60

Ser Ala Asn Gly Pro Ser Arg Glu Gly Ser Arg Leu Pro Pro Ala Arg
65                  70                  75                  80

Glu Gly His Pro Val Tyr Pro Gln Leu Arg Pro Gly Tyr Ile Pro Ile
                85                  90                  95

Pro Val Leu His Glu Gly Ala Glu Asn Arg Gln Val His Pro Phe His
            100                 105                 110

Val Tyr Pro Gln Pro Gly Met Gln Arg Phe Arg Thr Glu Ala Ala Ala
        115                 120                 125

Ala Ala Pro Gln Arg Ser Gln Ser Pro Leu Arg Gly Met Pro Glu Thr
130                 135                 140

Thr Gln Pro Asp Lys Gln Cys Gly Gln Val Ala Ala Ala Ala Ala Ala
145                 150                 155                 160

Gln Pro Pro Ala Ser His Gly Pro Glu Arg Ser Gln Ser Pro Ala Ala
                165                 170                 175

Ser Asp Cys Ser Ser Ser Ser Ser Ala Ser Leu Pro Ser Ser Gly
            180                 185                 190

Arg Ser Ser Leu Gly Ser His Gln Leu Pro Arg Gly Tyr Ile Ser Ile
        195                 200                 205

Pro Val Ile His Glu Gln Asn Val Thr Arg Pro Ala Ala Gln Pro Ser
    210                 215                 220

Phe His Gln Ala Gln Lys Thr His Tyr Pro Ala Gln Gln Gly Glu Tyr
225                 230                 235                 240

Gln Thr His Gln Pro Val Tyr His Lys Ile Gln Gly Asp Asp Trp Glu
                245                 250                 255

Pro Arg Pro Leu Arg Ala Ala Ser Pro Phe Arg Ser Ser Val Gln Gly
            260                 265                 270

Ala Ser Ser Arg Glu Gly Ser Pro Ala Arg Ser Ser Thr Pro Leu His
        275                 280                 285

Ser Pro Ser Pro Ile Arg Val His Thr Val Val Asp Arg Pro Gln Gln
    290                 295                 300

Pro Met Thr His Arg Glu Thr Ala Pro Val Ser Gln Pro Glu Asn Lys
305                 310                 315                 320

Pro Glu Ser Lys Pro Gly Pro Val Gly Pro Glu Leu Pro Pro Gly His
                325                 330                 335

Ile Pro Ile Gln Val Ile Arg Lys Glu Val Asp Ser Lys Pro Val Ser
            340                 345                 350

Gln Lys Pro Pro Pro Ser Glu Lys Val Glu Val Lys Val Pro Pro
        355                 360                 365

Ala Pro Val Pro Cys Pro Pro Ser Pro Gly Pro Ser Ala Val Pro
    370                 375                 380

Ser Ser Pro Lys Ser Val Ala Thr Glu Glu Arg Ala Ala Pro Ser Thr
385                 390                 395                 400
```

```
Ala Pro Ala Glu Ala Thr Leu Pro Lys Pro Gly Glu Ala Glu Ala Pro
            405                 410                 415

Pro Lys His Pro Gly Val Leu Lys Val Glu Ala Ile Leu Glu Lys Val
        420                 425                 430

Gln Gly Leu Glu Gln Ala Val Asp Asn Phe Glu Gly Lys Lys Thr Asp
            435                 440                 445

Lys Lys Tyr Leu Met Ile Glu Glu Tyr Leu Thr Lys Glu Leu Leu Ala
450                 455                 460

Leu Asp Ser Val Asp Pro Glu Gly Arg Ala Asp Val Arg Gln Ala Arg
465                 470                 475                 480

Arg Asp Gly Val Arg Lys Val Gln Thr Ile Leu Glu Lys Leu Glu Gln
                485                 490                 495

Lys Ala Ile Asp Val Pro Gly Gln Val Gln Val Tyr Glu Leu Gln Pro
            500                 505                 510

Ser Asn Leu Glu Ala Asp Gln Pro Leu Gln Ala Ile Met Glu Met Gly
            515                 520                 525

Ala Val Ala Ala Asp Lys Gly Lys Lys Asn Ala Gly Asn Ala Glu Asp
            530                 535                 540

Pro His Thr Glu Thr Gln Gln Pro Glu Ala Thr Ala Ala Ala Thr Ser
545                 550                 555                 560

Asn Pro Ser Ser Met Thr Asp Thr Pro Gly Asn Pro Ala Ala Pro
                565                 570                 575

<210> SEQ ID NO 5
<211> LENGTH: 574
<212> TYPE: PRT
<213> ORGANISM: Homo sapiens

<400> SEQUENCE: 5

Met Ser Ala Ala Thr His Ser Pro Met Met Gln Val Ala Ser Gly Asn
1               5                   10                  15

Gly Asp Arg Asp Pro Leu Pro Pro Gly Trp Glu Ile Lys Ile Asp Pro
            20                  25                  30

Gln Thr Gly Trp Pro Phe Phe Val Asp His Asn Ser Arg Thr Thr Thr
        35                  40                  45

Trp Asn Asp Pro Arg Val Pro Ser Glu Gly Pro Lys Glu Thr Pro Ser
50                  55                  60

Ser Ala Asn Gly Pro Ser Arg Glu Gly Ser Arg Leu Pro Pro Ala Arg
65                  70                  75                  80

Glu Gly His Pro Val Tyr Pro Gln Leu Arg Pro Gly Tyr Ile Pro Ile
                85                  90                  95

Pro Val Leu His Glu Gly Ala Glu Asn Arg Gln Val His Pro Phe His
            100                 105                 110

Val Tyr Pro Gln Pro Gly Met Gln Arg Phe Arg Thr Glu Ala Ala Ala
        115                 120                 125

Ala Ala Pro Gln Arg Ser Gln Ser Pro Leu Arg Gly Met Pro Glu Thr
130                 135                 140

Thr Gln Pro Asp Lys Gln Cys Gly Gln Val Ala Ala Ala Ala Ala Ala
145                 150                 155                 160

Gln Pro Pro Ala Ser His Gly Pro Glu Arg Ser Gln Ser Pro Ala Ala
                165                 170                 175

Ser Asp Cys Ser Ser Ser Ser Ser Ala Ser Leu Pro Ser Ser Gly
            180                 185                 190

Arg Ser Ser Leu Gly Ser His Gln Leu Pro Arg Gly Tyr Ile Ser Ile
        195                 200                 205
```

Pro Val Ile His Glu Gln Asn Val Thr Arg Pro Ala Ala Gln Pro Ser
210                 215                 220

Phe His Gln Ala Gln Lys Thr His Tyr Pro Ala Gln Gln Gly Glu Tyr
225                 230                 235                 240

Gln Thr His Gln Pro Val Tyr His Lys Ile Gln Gly Asp Asp Trp Glu
            245                 250                 255

Pro Arg Pro Leu Arg Ala Ala Ser Pro Phe Arg Ser Ser Val Gln Gly
        260                 265                 270

Ala Ser Ser Arg Glu Gly Ser Pro Ala Arg Ser Ser Thr Pro Leu His
    275                 280                 285

Ser Pro Ser Pro Ile Arg Val His Thr Val Val Asp Arg Pro Gln Pro
290                 295                 300

Met Thr His Arg Glu Thr Ala Pro Val Ser Gln Pro Glu Asn Lys Pro
305                 310                 315                 320

Glu Ser Lys Pro Gly Pro Val Gly Pro Glu Leu Pro Pro Gly His Ile
            325                 330                 335

Pro Ile Gln Val Ile Arg Lys Glu Val Asp Ser Lys Pro Val Ser Gln
        340                 345                 350

Lys Pro Pro Pro Ser Glu Lys Val Glu Val Lys Val Pro Pro Ala
    355                 360                 365

Pro Val Pro Cys Pro Pro Ser Pro Gly Pro Ser Ala Val Pro Ser
370                 375                 380

Ser Pro Lys Ser Val Ala Thr Glu Glu Arg Ala Ala Pro Ser Thr Ala
385                 390                 395                 400

Pro Ala Glu Ala Thr Leu Pro Lys Pro Gly Ala Glu Ala Pro Pro
            405                 410                 415

Lys His Pro Gly Val Leu Lys Val Glu Ala Ile Leu Glu Lys Val Gln
        420                 425                 430

Gly Leu Glu Gln Ala Val Asp Asn Phe Glu Gly Lys Lys Thr Asp Lys
    435                 440                 445

Lys Tyr Leu Met Ile Glu Glu Tyr Leu Thr Lys Glu Leu Leu Ala Leu
450                 455                 460

Asp Ser Val Asp Pro Glu Gly Arg Ala Asp Val Arg Gln Ala Arg Arg
465                 470                 475                 480

Asp Gly Val Arg Lys Val Gln Thr Ile Leu Glu Lys Leu Glu Gln Lys
            485                 490                 495

Ala Ile Asp Val Pro Gly Gln Val Gln Val Tyr Glu Leu Gln Pro Ser
        500                 505                 510

Asn Leu Glu Ala Asp Gln Pro Leu Gln Ala Ile Met Glu Met Gly Ala
    515                 520                 525

Val Ala Ala Asp Lys Gly Lys Lys Asn Ala Gly Asn Ala Glu Asp Pro
530                 535                 540

His Thr Glu Thr Gln Gln Pro Glu Ala Thr Ala Ala Thr Ser Asn
545                 550                 555                 560

Pro Ser Ser Met Thr Asp Thr Pro Gly Asn Pro Ala Ala Pro
            565                 570

<210> SEQ ID NO 6
<211> LENGTH: 575
<212> TYPE: PRT
<213> ORGANISM: Homo sapiens

<400> SEQUENCE: 6

Met Ser Ala Ala Thr His Ser Pro Met Met Gln Val Ala Ser Gly Asn

-continued

```
1               5                   10                  15
Gly Asp Arg Asp Pro Leu Pro Pro Gly Trp Glu Ile Lys Ile Asp Pro
                20                  25                  30

Gln Thr Gly Trp Pro Phe Phe Val Asp His Asn Ser Arg Thr Thr Thr
            35                  40                  45

Trp Asn Asp Pro Arg Val Pro Ser Glu Gly Pro Lys Glu Thr Pro Ser
50                      55                  60

Ser Ala Asn Gly Pro Ser Arg Glu Gly Ser Arg Leu Pro Pro Ala Arg
65                  70                  75                  80

Glu Gly His Pro Val Tyr Pro Gln Leu Arg Pro Gly Tyr Ile Pro Ile
                85                  90                  95

Pro Val Leu His Glu Gly Ala Glu Asn Arg Gln Val His Pro Phe His
                100                 105                 110

Val Tyr Pro Gln Pro Gly Met Gln Arg Phe Arg Thr Glu Ala Ala Ala
            115                 120                 125

Ala Ala Pro Gln Arg Ser Gln Ser Pro Leu Arg Gly Met Pro Glu Thr
130                 135                 140

Thr Gln Pro Asp Lys Gln Cys Gly Gln Val Ala Ala Ala Ala Ala Ala
145                 150                 155                 160

Gln Pro Pro Ala Ser His Gly Pro Glu Arg Ser Gln Ser Pro Ala Ala
                165                 170                 175

Ser Asp Cys Ser Ser Ser Ser Ser Ala Ser Leu Pro Ser Ser Gly
                180                 185                 190

Arg Ser Ser Leu Gly Ser His Gln Leu Pro Arg Gly Tyr Ile Ser Ile
            195                 200                 205

Pro Val Ile His Glu Gln Asn Val Thr Arg Pro Ala Ala Gln Pro Ser
210                 215                 220

Phe His Gln Ala Gln Lys Thr His Tyr Pro Ala Gln Gln Gly Glu Tyr
225                 230                 235                 240

Gln Thr His Gln Pro Val Tyr His Lys Ile Gln Gly Asp Asp Trp Glu
                245                 250                 255

Pro Arg Pro Leu Arg Ala Ala Ser Pro Phe Arg Ser Ser Val Gln Gly
            260                 265                 270

Ala Ser Ser Arg Glu Gly Ser Pro Ala Arg Ser Ser Thr Pro Leu His
        275                 280                 285

Ser Pro Ser Pro Ile Arg Val His Thr Val Val Asp Arg Pro Gln Gln
290                 295                 300

Pro Met Thr His Arg Glu Thr Ala Pro Val Ser Gln Pro Glu Asn Lys
305                 310                 315                 320

Pro Glu Ser Lys Pro Gly Pro Val Gly Pro Glu Leu Pro Pro Gly His
                325                 330                 335

Ile Pro Ile Gln Val Ile Arg Lys Glu Val Asp Ser Lys Pro Val Ser
            340                 345                 350

Gln Lys Pro Pro Pro Ser Glu Lys Val Glu Val Lys Val Pro Pro
                355                 360                 365

Ala Pro Val Pro Cys Pro Pro Ser Pro Gly Pro Ser Ala Val Pro
            370                 375                 380

Ser Ser Pro Lys Ser Val Ala Thr Glu Glu Arg Ala Ala Pro Ser Thr
385                 390                 395                 400

Ala Pro Ala Glu Ala Thr Pro Pro Lys Pro Gly Glu Ala Glu Ala Pro
                405                 410                 415

Pro Lys His Pro Gly Val Leu Lys Val Glu Ala Ile Leu Glu Lys Val
                420                 425                 430
```

```
Gln Gly Leu Glu Gln Ala Val Asp Asn Phe Glu Gly Lys Lys Thr Asp
        435                 440                 445

Lys Lys Tyr Leu Met Ile Glu Glu Tyr Leu Thr Lys Glu Leu Leu Ala
    450                 455                 460

Leu Asp Ser Val Asp Pro Glu Gly Arg Ala Asp Val Arg Gln Ala Arg
465                 470                 475                 480

Arg Asp Gly Val Arg Lys Val Gln Thr Ile Leu Glu Lys Leu Glu Gln
                485                 490                 495

Lys Ala Ile Asp Val Pro Gly Gln Val Gln Val Tyr Glu Leu Gln Pro
            500                 505                 510

Ser Asn Leu Glu Ala Asp Gln Pro Leu Gln Ala Ile Met Glu Met Gly
        515                 520                 525

Ala Val Ala Ala Asp Lys Gly Lys Lys Asn Ala Gly Asn Ala Glu Asp
    530                 535                 540

Pro His Thr Glu Thr Gln Gln Pro Glu Ala Thr Ala Ala Ala Thr Ser
545                 550                 555                 560

Asn Pro Ser Ser Met Thr Asp Thr Pro Gly Asn Pro Ala Ala Pro
                565                 570                 575

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide linker

<400> SEQUENCE: 7

Gly Gly Gly Gly Ser Gly Gly Gly Ser Gly Gly Gly Gly Ser
1               5                   10                  15

<210> SEQ ID NO 8
<211> LENGTH: 13
<212> TYPE: PRT
<213> ORGANISM: Homo sapiens

<400> SEQUENCE: 8

Lys Pro Ser Trp Arg Arg Tyr Arg Gly Trp Ser Arg Leu
1               5                   10

<210> SEQ ID NO 9
<211> LENGTH: 85
<212> TYPE: DNA
<213> ORGANISM: Homo sapiens

<400> SEQUENCE: 9
aaaaccagga gaagccgagg ctcccccaaa acatccagga gtgctgaaag tggaagccat      60
cctggagaag gtacaggggc tggag                                           85

<210> SEQ ID NO 10
<211> LENGTH: 64
<212> TYPE: DNA
<213> ORGANISM: Homo sapiens

<400> SEQUENCE: 10
aaaaccagga gaagccgagg ctcccccaaa acatccagga gtgctgaaag tggaagccat      60
cctg                                                                  64

<210> SEQ ID NO 11
<211> LENGTH: 10
```

<212> TYPE: DNA
<213> ORGANISM: Homo sapiens

<400> SEQUENCE: 11
aggggctgga                                                         10

<210> SEQ ID NO 12
<211> LENGTH: 64
<212> TYPE: DNA
<213> ORGANISM: Homo sapiens

<400> SEQUENCE: 12
aaaaccagga gaagccgagg ctcccccaaa acatccagga gtgaagccat cctggagaag    60
gtac                                                               64

<210> SEQ ID NO 13
<211> LENGTH: 64
<212> TYPE: DNA
<213> ORGANISM: Homo sapiens

<400> SEQUENCE: 13
aaaaccagga gaagccgagg ctcccccaaa acatccagga gtgaagccat cctggagaag    60
gtac                                                               64

<210> SEQ ID NO 14
<211> LENGTH: 65
<212> TYPE: DNA
<213> ORGANISM: Homo sapiens

<400> SEQUENCE: 14
aaaaccagga gaagccgagg ctcccccaaa acatccagga gtgctgaaag tggaagccat    60
cctgg                                                              65

<210> SEQ ID NO 15
<211> LENGTH: 66
<212> TYPE: DNA
<213> ORGANISM: Homo sapiens

<400> SEQUENCE: 15
aaaaccagga gaagccgagg ctcccccaaa acatccagga gtgctgaaag tggaagccat    60
cctgga                                                             66

<210> SEQ ID NO 16
<211> LENGTH: 71
<212> TYPE: DNA
<213> ORGANISM: Homo sapiens

<400> SEQUENCE: 16
aaaaccagga gaagccgagg ctcccccaaa acatccagga gtgaagccat cctggagaag    60
gtacaggggc t                                                       71

<210> SEQ ID NO 17
<211> LENGTH: 72
<212> TYPE: DNA
<213> ORGANISM: Homo sapiens

<400> SEQUENCE: 17
aaaaccagga gaagccgagg ctcccccaaa acatccagga gtgaagccat cctggagaag    60
gtacaggggc tg                                                      72

```
<210> SEQ ID NO 18
<211> LENGTH: 68
<212> TYPE: DNA
<213> ORGANISM: Homo sapiens

<400> SEQUENCE: 18
aaaaccagga gaagccgagg ctcccccaaa acatccagga gtgctgaaag tggaagccat      60
cctggaga                                                              68

<210> SEQ ID NO 19
<211> LENGTH: 73
<212> TYPE: DNA
<213> ORGANISM: Homo sapiens

<400> SEQUENCE: 19
aaaaccagga gaagccgagg ctcccccaaa acatccagga gtgctgaaag tggaagccat      60
cctggagaag gta                                                        73

<210> SEQ ID NO 20
<211> LENGTH: 73
<212> TYPE: DNA
<213> ORGANISM: Homo sapiens

<400> SEQUENCE: 20
aaaaccagga gaagccgagg ctcccccaaa acatccagga gtgctgaaag tggaagccat      60
cctggacaag gta                                                        73

<210> SEQ ID NO 21
<211> LENGTH: 70
<212> TYPE: DNA
<213> ORGANISM: Homo sapiens

<400> SEQUENCE: 21
aaaaccagga gaagccgagg ctcccccaaa acatccagga gtgctgaaag tggaagccat      60
cctggagaag                                                            70

<210> SEQ ID NO 22
<211> LENGTH: 75
<212> TYPE: DNA
<213> ORGANISM: Homo sapiens

<400> SEQUENCE: 22
aaaaccagga gaagccgagg ctcccccaaa acatccagga gtgaagccat cctggagaag      60
gtacaggggc tggag                                                      75

<210> SEQ ID NO 23
<211> LENGTH: 75
<212> TYPE: DNA
<213> ORGANISM: Homo sapiens

<400> SEQUENCE: 23
aaaaccagga gaagccgagg ctcccccaaa acatccagga gtgaagccat cctggagaag      60
gtacaggggc tggag                                                      75

<210> SEQ ID NO 24
<211> LENGTH: 84
<212> TYPE: DNA
<213> ORGANISM: Homo sapiens

<400> SEQUENCE: 24
```
aaaaccagga gaagccgagg ctcccccaaa acatccagga gtgctgaaag tggaagccat    60
cctggagaag gtacaggggc tgga                                          84

<210> SEQ ID NO 25
<211> LENGTH: 75
<212> TYPE: DNA
<213> ORGANISM: Homo sapiens

<400> SEQUENCE: 25
aaaaccagga gaagccgagg ctcccccaaa acatccagga gtgaagccat cctggagaag    60
gtacaggggc tggag                                                    75

<210> SEQ ID NO 26
<211> LENGTH: 82
<212> TYPE: DNA
<213> ORGANISM: Homo sapiens

<400> SEQUENCE: 26
aaaaccagga gaagccgagg ctcccccaaa acatccagga gtgctgaaag tggaagccat    60
cctggagaag gtacaggggc tg                                            82

<210> SEQ ID NO 27
<211> LENGTH: 75
<212> TYPE: DNA
<213> ORGANISM: Homo sapiens

<400> SEQUENCE: 27
aaaaccagga gaagccgagg ctcccccaaa acatccagga gtgaagccat cctggagaag    60
gtacaggggc tggag                                                    75

<210> SEQ ID NO 28
<211> LENGTH: 85
<212> TYPE: DNA
<213> ORGANISM: Homo sapiens

<400> SEQUENCE: 28
aaaaccagga gaagccgagg ctcccccaaa acatccagga gtgctgaaag tggaagccat    60
cctggagaag gtacaggggc tggag                                         85

<210> SEQ ID NO 29
<211> LENGTH: 75
<212> TYPE: DNA
<213> ORGANISM: Homo sapiens

<400> SEQUENCE: 29
aaaaccagga gaagccgagg ctcccccaaa acatccagga gtgaagccat cctggagaag    60
gtacaggggc tggag                                                    75

<210> SEQ ID NO 30
<211> LENGTH: 85
<212> TYPE: DNA
<213> ORGANISM: Homo sapiens

<400> SEQUENCE: 30
aaaaccagga gaagccgagg ctcccccaaa acatccagga gtgctgaaag tggaagccat    60
cctggagaag gtacaggggc tggag                                         85

<210> SEQ ID NO 31

<211> LENGTH: 74
<212> TYPE: DNA
<213> ORGANISM: Homo sapiens

<400> SEQUENCE: 31
aaaaccagga gaagccgagg ctcccccgaaa acatccagga gtgctgaaag tggaagccat    60
cctggagaag gtac                                                      74

<210> SEQ ID NO 32
<211> LENGTH: 85
<212> TYPE: DNA
<213> ORGANISM: Homo sapiens

<400> SEQUENCE: 32
aaaaccagga gaagccgagg ctcccccaaa acatccagga gtgctgaaag tggaagccat    60
cctggagaag gtacaggggc tggag                                          85

<210> SEQ ID NO 33
<211> LENGTH: 85
<212> TYPE: DNA
<213> ORGANISM: Homo sapiens

<400> SEQUENCE: 33
aaaaccagga gaagccgagg ctcccccaaa acatccagga gtgctgaaag tggaagccat    60
cctggagaag gtacaggggc tggag                                          85

<210> SEQ ID NO 34
<211> LENGTH: 75
<212> TYPE: DNA
<213> ORGANISM: Homo sapiens

<400> SEQUENCE: 34
aaaaccagga gaagccgagg ctcccccaaa acatccagga gtgaagccat cctggagaag    60
gtacaggggc tggag                                                     75

<210> SEQ ID NO 35
<211> LENGTH: 80
<212> TYPE: DNA
<213> ORGANISM: Homo sapiens

<400> SEQUENCE: 35
caggagaagc cgaggctccc ccaaaacatc caggagtgct gaaagtggaa gccatcctgg    60
agaaggtaca ggggctggca                                                80

<210> SEQ ID NO 36
<211> LENGTH: 64
<212> TYPE: DNA
<213> ORGANISM: Homo sapiens

<400> SEQUENCE: 36
aagccgaggc tcccccaaaa catccaggag tgaagccatc ctggagaagg tacaggggct    60
ggag                                                                 64

<210> SEQ ID NO 37
<211> LENGTH: 63
<212> TYPE: DNA
<213> ORGANISM: Homo sapiens
<220> FEATURE:
<221> NAME/KEY: modified_base
<222> LOCATION: (4)..(4)
<223> OTHER INFORMATION: n is a, c, g or t

<400> SEQUENCE: 37
agcngaggct cccccaaaac atccaggagt gaagccatcc tggacaaggt acaggggctg    60
gag    63

<210> SEQ ID NO 38
<211> LENGTH: 70
<212> TYPE: DNA
<213> ORGANISM: Homo sapiens

<400> SEQUENCE: 38
cgaggctccc ccaaaacatc caggagtgct gaaagtggaa gccatcctgg agaaggtaca    60
ggggctggag    70

<210> SEQ ID NO 39
<211> LENGTH: 58
<212> TYPE: DNA
<213> ORGANISM: Homo sapiens

<400> SEQUENCE: 39
aggctccccc aaaacatcca ggagtgaagc catcctggag aaggtacagg ggctggag    58

<210> SEQ ID NO 40
<211> LENGTH: 67
<212> TYPE: DNA
<213> ORGANISM: Homo sapiens

<400> SEQUENCE: 40
ggctccccca aaacatccag gagtgctgaa agtggaagcc atcctggaga aggtacaggg    60
gctggag    67

<210> SEQ ID NO 41
<211> LENGTH: 66
<212> TYPE: DNA
<213> ORGANISM: Homo sapiens

<400> SEQUENCE: 41
gctcccccaa aacatccagg agtgctgaaa gtggaagcca tcctggagaa ggtacagggg    60
ctggag    66

<210> SEQ ID NO 42
<211> LENGTH: 54
<212> TYPE: DNA
<213> ORGANISM: Homo sapiens

<400> SEQUENCE: 42
tcccccaaaa catccaggag tgaagccatc ctggagaagg tacaggggct ggag    54

<210> SEQ ID NO 43
<211> LENGTH: 62
<212> TYPE: DNA
<213> ORGANISM: Homo sapiens

<400> SEQUENCE: 43
ccccaaaaca tccaggagtg ctgaaagtgg aagccatcct ggagaaggta cagggctgg    60 ag    62

<210> SEQ ID NO 44
<211> LENGTH: 47
<212> TYPE: DNA

<213> ORGANISM: Homo sapiens

<400> SEQUENCE: 44
gagtgctgaa agtggaagcc atcctggaga aggtacaggg gctggag     47

<210> SEQ ID NO 45
<211> LENGTH: 43
<212> TYPE: DNA
<213> ORGANISM: Homo sapiens
<220> FEATURE:
<221> NAME/KEY: modified_base
<222> LOCATION: (4)..(4)
<223> OTHER INFORMATION: n is a, c, g or t

<400> SEQUENCE: 45
atcnaggagt gaagccatcc tggagaaggt acaggggctg gag     43

<210> SEQ ID NO 46
<211> LENGTH: 40
<212> TYPE: DNA
<213> ORGANISM: Homo sapiens

<400> SEQUENCE: 46
gaaagtggaa gccatcctgg agaaggtaca ggggctggag     40

<210> SEQ ID NO 47
<211> LENGTH: 39
<212> TYPE: DNA
<213> ORGANISM: Homo sapiens

<400> SEQUENCE: 47
aggagtgaag ccatcctgga gaaggtacag gggctggag     39

<210> SEQ ID NO 48
<211> LENGTH: 37
<212> TYPE: DNA
<213> ORGANISM: Homo sapiens

<400> SEQUENCE: 48
agtggaagcc atcctggaga aggtacaggg gctggag     37

<210> SEQ ID NO 49
<211> LENGTH: 34
<212> TYPE: DNA
<213> ORGANISM: Homo sapiens

<400> SEQUENCE: 49
tgaagccatc ctggagaagg tacaggggct ggag     34

<210> SEQ ID NO 50
<211> LENGTH: 31
<212> TYPE: DNA
<213> ORGANISM: Homo sapiens

<400> SEQUENCE: 50
aaacatccag gagtgctgaa agtggaagcc a     31

```
<210> SEQ ID NO 51
<211> LENGTH: 30
<212> TYPE: DNA
<213> ORGANISM: Homo sapiens

<400> SEQUENCE: 51
aaacatccag gagtgmwgmm akyskrrrcc                                            30
```